United States Patent [19]

Shibata et al.

[11] Patent Number: 5,631,222
[45] Date of Patent: May 20, 1997

[54] ENDOTHELIN-ANTAGONIZING PEPTIDE

[75] Inventors: Kenji Shibata, Kawasaki; Toshiyuki Suzawa, Yamato; Motoo Yamasaki; Takeo Tanaka, both of Machida; Eiji Tsukuda, Shimotogari; Koji Yamada, Sagamihara; Tetsuji Ohno, Shimotogari, all of Japan

[73] Assignee: Kyowa Hakko Kogyo Co., Ltd., Tokyo, Japan

[21] Appl. No.: 382,013

[22] PCT Filed: Jun. 23, 1994

[86] PCT No.: PCT/JP94/01011

§ 371 Date: Feb. 10, 1995

§ 102(e) Date: Feb. 10, 1995

[87] PCT Pub. No.: WO95/00546

PCT Pub. Date: May 1, 1995

[30] Foreign Application Priority Data

Jun. 25, 1993 [JP] Japan ................................. 5-155031

[51] Int. Cl.$^6$ ............................. A61K 38/00; C07K 7/08; C07K 5/12

[52] U.S. Cl. ................................. 514/9; 514/11; 530/317; 530/326

[58] Field of Search ...................... 514/13, 9, 11; 530/326, 317

[56] References Cited

U.S. PATENT DOCUMENTS

| 5,231,166 | 7/1993 | Masaki et al. | 530/324 |
| 5,294,569 | 3/1994 | Masaki et al. | 530/324 |
| 5,306,808 | 4/1994 | Wakimasu et al. | 530/326 |
| 5,352,659 | 10/1994 | Wakimasu et al. | 530/326 |
| 5,382,569 | 1/1995 | Cody et al. | 514/17 |

*Primary Examiner*—Cecilia J. Tsang
*Assistant Examiner*—S. G. Marshall
*Attorney, Agent, or Firm*—White & Case

[57] ABSTRACT

Disclosed is a peptide compound represented by the following formula (I):

$$R^1-R^2-R^3-R^4-R^5-R^6-R^7-R^8-R^9-R^{10}-R^{11}-R^{12}-Phe-R^{14}-R^{15}-R^{16}-R^{17}-R^{18}-Ile-R^{20}-Z \text{ SEQ. ID NO. 64,} \quad (I)$$

wherein $R^{1-12}$, $R^{14-18}$, and $R^{20}$ are as defined in the specification.

9 Claims, No Drawings

SEQUENCE LISTING ( 1 ) GENERAL INFORMATION:

( i i i ) NUMBER OF SEQUENCES: 76

( 2 ) INFORMATION FOR SEQ ID NO:1:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( C ) IDENTIFICATION METHOD: by experiment
    ( D ) OTHER INFORMATION: /label=Xaa
        / note= "Nalpha-succinylglycine"

( x i ) SEQUENCE DESCRIPTION: SEQ ID NO:1:

```
Xaa  Asn  Trp  His  Gly  Thr  Ala  Pro  Asp  Trp  Val  Tyr  Phe  Ala  His  Leu
1                   5                        10                       15

Asp  Ile  Ile  Trp
                20
```

( 2 ) INFORMATION FOR SEQ ID NO:2:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

```
Gly  Asn  Trp  His  Thr  Thr  Ala  Pro  Asp  Trp  Val  Tyr  Phe  Ala  His  Leu
1                   5                        10                       15

Asp  Ile  Ile  Trp
                20
```

( 2 ) INFORMATION FOR SEQ ID NO:3:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

Gly Asn Trp His Gly Gly Ala Pro Asp Trp Val Tyr Phe Ala His Leu
1               5                   10                  15

Asp Ile Ile Trp
            20

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Gly Asn Trp His Gly Thr Ala Pro Asp Ala Val Tyr Phe Ala His Leu
1               5                   10                  15

Asp Ile Ile Trp
            20

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Gly Asn Trp His Gly Thr Ala Pro Asp Trp Val Tyr Phe Ala His Leu
1               5                   10                  15

Asp Ile Ile Phe
            20

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Gly Asp Trp Lys Gly Thr Ser Pro Asp Trp Val Tyr Phe Ala His Leu
1               5                   10                  15

Asp Ile Ile Trp
            20

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Asn Trp His Gly Thr Ala Pro Asp Trp Val Tyr Phe Ala His Leu Asp
1               5                   10                  15

Ile Ile Trp (2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Trp His Gly Thr Ala Pro Asp Trp Val Tyr Phe Ala His Leu Asp Ile
1               5                   10                  15
Ile Trp (2) INFORMATION FOR SEQ ID NO:9:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

His Gly Thr Ala Pro Asp Trp Val Tyr Phe Ala His Leu Asp Ile Ile
1               5                   10                  15
Trp (2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gly Asn Trp His Gly Thr Ala Pro Asp Trp Tyr Phe Ala His Leu Asp
1               5                   10                  15
Ile Ile Trp (2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Gly Asn Trp His Gly Thr Ala Pro Asp Trp Phe Ala His Leu Asp Ile
1               5                   10                  15
Ile Trp (2) INFORMATION FOR SEQ ID NO:12:

(i) SEQUENCE CHARACTERISTICS:
        (A) LENGTH: 11 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Trp Val Tyr Phe Ala His Leu Asp Ile Ile Trp
    1               5                   10

(2) INFORMATION FOR SEQ ID NO:13:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Gly Asn Trp His Gly Thr Ala Pro Asp Trp Val Tyr Phe Ala His Leu
    1               5                   10                  15

Thr Leu Ile Trp
                20

(2) INFORMATION FOR SEQ ID NO:14:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 18
            (C) IDENTIFICATION METHOD: by experiment
            (D) OTHER INFORMATION: /label=Xaa
                    / note= "beta-cyclohexyl-L-alanine"

(xi) SEQUENCE DESCRIPTION: SEQ ID NO:14:

Gly Asn Trp His Gly Thr Ala Pro Asp Trp Val Tyr Phe Ala His Leu
    1               5                   10                  15

Thr Xaa Ile Trp
                20

(2) INFORMATION FOR SEQ ID NO:15:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 18
            (C) IDENTIFICATION METHOD: by experiment
            (D) OTHER INFORMATION: /label=Xaa
                    / note= "L-2-aminobutanoic acid"

(xi) SEQUENCE DESCRIPTION: SEQ ID NO:15:

Gly Asn Trp His Gly Thr Ala Pro Asp Trp Val Tyr Phe Ala His Leu
    1               5                   10                  15

Thr Xaa Ile Trp (2) INFORMATION FOR SEQ ID NO:16:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:16:

Gly Asn Trp His Gly Thr Ala Pro Asp Trp Val Tyr Phe Ala His Leu
1               5                   10                  15
Asp Leu Ile Trp
            20

(2) INFORMATION FOR SEQ ID NO:17:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 18
    (C) IDENTIFICATION METHOD: by experiment
    (D) OTHER INFORMATION: /label=Xaa
        /note= "beta-(2-thienyl)-L-alanine"

(xi) SEQUENCE DESCRIPTION: SEQ ID NO:17:

Gly Asn Trp His Gly Thr Ala Pro Asp Trp Val Tyr Phe Ala His Leu
1               5                   10                  15
Thr Xaa Ile Trp
            20

(2) INFORMATION FOR SEQ ID NO:18:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:18:

Gly Asn Trp His Gly Thr Ala Pro Asp Trp Val Tyr Phe Ala His Leu
1               5                   10                  15
Thr Met Ile Trp
            20

(2) INFORMATION FOR SEQ ID NO:19:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:19:

Gly Asn Trp His Gly Thr Ala Pro Asp Trp Val Tyr Phe Ala His Leu

Thr Tyr Ile Trp
            20

( 2 ) INFORMATION FOR SEQ ID NO:20:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Gly Asn Trp His Gly Thr Ala Pro Asp Trp Val Tyr Phe Ala His Leu
1               5                   10                  15

Asn Tyr Ile Trp
            20

( 2 ) INFORMATION FOR SEQ ID NO:21:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Gly Asn Trp His Gly Thr Ala Pro Asp Trp Val Tyr Phe Ala His Leu
1               5                   10                  15

Ser Met Ile Trp
            20

( 2 ) INFORMATION FOR SEQ ID NO:22:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 18
        ( C ) IDENTIFICATION METHOD: by experiment
        ( D ) OTHER INFORMATION: /label=Xaa
            / note= "beta-(2-thienyl)-L-alanine"

( x i ) SEQUENCE DESCRIPTION: SEQ ID NO:22:

Gly Asp Trp Lys Gly Thr Ser Pro Asp Trp Val Tyr Phe Ala His Leu
1               5                   10                  15

Thr Xaa Ile Trp
            20

( 2 ) INFORMATION FOR SEQ ID NO:23:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 18
    ( C ) IDENTIFICATION METHOD: by experiment
    ( D ) OTHER INFORMATION: /label=Xaa
        / note= "N-methyl-L-leucine"

( x i ) SEQUENCE DESCRIPTION: SEQ ID NO:23:

```
Gly Asn Trp His Gly Thr Ala Pro Asp Trp Val Tyr Phe Ala His Leu
 1               5                   10                  15
Thr Xaa Ile Trp
            20
```

( 2 ) INFORMATION FOR SEQ ID NO:24:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 18
        ( C ) IDENTIFICATION METHOD: by experiment
        ( D ) OTHER INFORMATION: /label=Xaa
            / note= "N-methyl-L-isoleucine"

( x i ) SEQUENCE DESCRIPTION: SEQ ID NO:24:

```
Gly Asn Trp His Gly Thr Ala Pro Asp Trp Val Tyr Phe Ala His Leu
 1               5                   10                  15
Thr Xaa Ile Trp
            20
```

( 2 ) INFORMATION FOR SEQ ID NO:25:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 18
        ( C ) IDENTIFICATION METHOD: by experiment
        ( D ) OTHER INFORMATION: /label=Xaa
            / note= "L-phenylglycine"

( x i ) SEQUENCE DESCRIPTION: SEQ ID NO:25:

```
Gly Asn Trp His Gly Thr Ala Pro Asp Trp Val Tyr Phe Ala His Leu
 1               5                   10                  15
Thr Xaa Ile Trp
            20
```

( 2 ) INFORMATION FOR SEQ ID NO:26:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site (B) LOCATION: 18
(C) IDENTIFICATION METHOD: by experiment
(D) OTHER INFORMATION: /label=Xaa
  / note= "L-norleucine"

(xi) SEQUENCE DESCRIPTION: SEQ ID NO:26:

Gly Asn Trp His Gly Thr Ala Pro Asp Trp Val Tyr Phe Ala His Leu
1               5                   10                  15

Thr Xaa Ile Trp
        20

(2) INFORMATION FOR SEQ ID NO:27:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 16
    (C) IDENTIFICATION METHOD: by experiment
    (D) OTHER INFORMATION: /label=Xaa
      / note= "L-norvaline"

(ix) FEATURE:
    (A) NAME/KEY: Modified-site
    (B) LOCATION: 18
    (C) IDENTIFICATION METHOD: by experiment
    (D) OTHER INFORMATION: /label=Xaa
      / note= "beta-(2-thienyl)-L-alanine"

(xi) SEQUENCE DESCRIPTION: SEQ ID NO:27:

Gly Asn Trp His Gly Thr Ala Pro Asp Trp Val Tyr Phe Ala His Xaa
1               5                   10                  15

Thr Xaa Ile Trp
        20

(2) INFORMATION FOR SEQ ID NO:28:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 18
    (C) IDENTIFICATION METHOD: by experiment
    (D) OTHER INFORMATION: /label=Xaa
      / note= "beta-(2-thienyl)-L-alanine"

(xi) SEQUENCE DESCRIPTION: SEQ ID NO:28:

Gly Asn Trp His Gly Thr Ala Pro Asp Trp Val Tyr Phe Ala His Leu
1               5                   10                  15

Gly Xaa Ile Trp
        20

(2) INFORMATION FOR SEQ ID NO:29:

(i) SEQUENCE CHARACTERISTICS:
    (A) LENGTH: 20 amino acids
    (B) TYPE: amino acid
    (C) STRANDEDNESS: single
    (D) TOPOLOGY: linear (  i i  ) MOLECULE TYPE: peptide (  x i  ) SEQUENCE DESCRIPTION: SEQ ID NO:29:

```
Cys Asn Trp His Gly Thr Ala Pro Cys Trp Val Tyr Phe Ala His Leu
1               5                   10                  15
Asp Ile Ile Trp
            20
```

( 2 ) INFORMATION FOR SEQ ID NO:30:

(  i  ) SEQUENCE CHARACTERISTICS:
       ( A ) LENGTH: 20 amino acids
       ( B ) TYPE: amino acid
       ( C ) STRANDEDNESS: single
       ( D ) TOPOLOGY: linear (  i i  ) MOLECULE TYPE: peptide (  i x  ) FEATURE:
       ( A ) NAME/KEY: Disulfide-bonds
       ( B ) LOCATION: 1..9
       ( C ) IDENTIFICATION METHOD: by experiment (  x i  ) SEQUENCE DESCRIPTION: SEQ ID NO:30:

```
Cys Asn Trp His Gly Thr Ala Pro Cys Trp Val Tyr Phe Ala His Leu
1               5                   10                  15
Asp Ile Ile Trp
            20
```

( 2 ) INFORMATION FOR SEQ ID NO:31:

(  i  ) SEQUENCE CHARACTERISTICS:
       ( A ) LENGTH: 20 amino acids
       ( B ) TYPE: amino acid
       ( C ) STRANDEDNESS: single
       ( D ) TOPOLOGY: linear (  i i  ) MOLECULE TYPE: peptide (  i x  ) FEATURE:
       ( A ) NAME/KEY: Modified-site
       ( B ) LOCATION: 18
       ( C ) IDENTIFICATION METHOD: by experiment
       ( D ) OTHER INFORMATION: /label=Xaa
                 / note= "beta-(2-thienyl)-L-alanine"

(  x i  ) SEQUENCE DESCRIPTION: SEQ ID NO:31:

```
Cys Asp Trp Lys Gly Thr Ser Pro Cys Trp Val Tyr Phe Ala His Leu
1               5                   10                  15
Thr Xaa Ile Trp
            20
```

( 2 ) INFORMATION FOR SEQ ID NO:32:

(  i  ) SEQUENCE CHARACTERISTICS:
       ( A ) LENGTH: 20 amino acids
       ( B ) TYPE: amino acid
       ( C ) STRANDEDNESS: single
       ( D ) TOPOLOGY: linear (  i i  ) MOLECULE TYPE: peptide (  i x  ) FEATURE:
       ( A ) NAME/KEY: Disulfide-bonds
       ( B ) LOCATION: 1..9
       ( C ) IDENTIFICATION METHOD: by experiment (  i x  ) FEATURE:
       ( A ) NAME/KEY: Modified-site
       ( B ) LOCATION: 18

(C) IDENTIFICATION METHOD: by experiment
(D) OTHER INFORMATION: /label=Xaa
/ note= "beta-(2-thienyl)-L-alanine"

(xi) SEQUENCE DESCRIPTION: SEQ ID NO:32:

Cys Asp Trp Lys Gly Thr Ser Pro Cys Trp Val Tyr Phe Ala His Leu
1               5                   10                  15
Thr Xaa Ile Trp
        20

(2) INFORMATION FOR SEQ ID NO:33:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:33:

Cys Asn Trp His Gly Thr Ala Pro Cys Trp Val Tyr Phe Ala His Leu
1               5                   10                  15
Thr Leu Ile Trp
        20

(2) INFORMATION FOR SEQ ID NO:34:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Disulfide-bonds
    (B) LOCATION: 1..9
    (C) IDENTIFICATION METHOD: by experiment (xi) SEQUENCE DESCRIPTION: SEQ ID NO:34:

Cys Asn Trp His Gly Thr Ala Pro Cys Trp Val Tyr Phe Ala His Leu
1               5                   10                  15
Thr Leu Ile Trp
        20

(2) INFORMATION FOR SEQ ID NO:35:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 18
    (C) IDENTIFICATION METHOD: by experiment
    (D) OTHER INFORMATION: /label=Xaa
        / note= "beta-cyclohexyl-L-alanine"

(xi) SEQUENCE DESCRIPTION: SEQ ID NO:35:

Cys Asn Trp His Gly Thr Ala Pro Cys Trp Val Tyr Phe Ala His Leu
1               5                   10                  15
Thr Xaa Ile Trp
        20

( 2 ) INFORMATION FOR SEQ ID NO:36:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Disulfide-bonds
        ( B ) LOCATION: 1..9
        ( C ) IDENTIFICATION METHOD: by experiment ( i x ) FEATURE:
        ( A ) NAME/KEY: Modified-site
        ( B ) LOCATION: 18
        ( C ) IDENTIFICATION METHOD: by experiment
        ( D ) OTHER INFORMATION: /label=Xaa
            / note= "beta-cyclohexyl-L-alanine"

( x i ) SEQUENCE DESCRIPTION: SEQ ID NO:36:

```
Cys  Asn  Trp  His  Gly  Thr  Ala  Pro  Cys  Trp  Val  Tyr  Phe  Ala  His  Leu
1                  5                         10                        15

Thr  Xaa  Ile  Trp
               20
```

( 2 ) INFORMATION FOR SEQ ID NO:37:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

```
Gly  Asn  Trp  His  Gly  Thr  Ala  Pro  Asp  Trp  Val  Tyr  Phe  Ala  His  Leu
1                  5                         10                        15

Glu  Ile  Ile  Trp
               20
```

( 2 ) INFORMATION FOR SEQ ID NO:38:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
Gly  Asn  Trp  His  Gly  Thr  Ala  Ala  Asp  Trp  Val  Tyr  Phe  Ala  His  Leu
1                  5                         10                        15

Ser  Met  Ile  Trp
               20
```

( 2 ) INFORMATION FOR SEQ ID NO:39:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

Gly Asn Trp His Gly Thr Ala Pro Asp Trp Pro Tyr Phe Ala His Leu
1               5                   10                  15

Asp Ile Ile Trp
            20

( 2 ) INFORMATION FOR SEQ ID NO:40:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 18
        ( C ) IDENTIFICATION METHOD: by experiment
        ( D ) OTHER INFORMATION: /label=Xaa
              / note= "beta-(2-thienyl)-L-alanine"

( x i ) SEQUENCE DESCRIPTION: SEQ ID NO:40:

Gly Asn Trp His Gly Thr Ala Pro Asp Trp Pro Tyr Phe Ala His Leu
1               5                   10                  15

Thr Xaa Ile Trp
            20

( 2 ) INFORMATION FOR SEQ ID NO:41:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
              / note=
              " Nalpha-(S-acetamidomethyl-beta-mercaptopropionyl
              ) - L-asparagine"

( x i ) SEQUENCE DESCRIPTION: SEQ ID NO:41:

Xaa Trp His Gly Thr Ala Pro Cys Trp Val Tyr Phe Ala His Leu Ser
1               5                   10                  15

Met Ile Trp ( 2 ) INFORMATION FOR SEQ ID NO:42:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

Gly Asn Trp His Gly Thr Ala Pro Asp Trp Val Tyr Phe Ala His Leu
1               5                   10                  15

Asp Ile Ile Trp
            20

( 2 ) INFORMATION FOR SEQ ID NO:43:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            " Nalpha-9-fluorenylmethyloxycarbonylglycine"

( x i ) SEQUENCE DESCRIPTION: SEQ ID NO:43:

```
Xaa  Asn  Trp  His  Gly  Thr  Ala  Pro
1                   5
```

( 2 ) INFORMATION FOR SEQ ID NO:44:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 10
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:44:

```
Gly  Asn  Trp  His  Gly  Thr  Ala  Pro  Asp  Xaa
1                   5                        10
```

( 2 ) INFORMATION FOR SEQ ID NO:45:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            " Nalpha-9-fluorenylmethyloxycarbonylglycine"

( i x ) FEATURE:
        ( A ) NAME/KEY: Modified-site
        ( B ) LOCATION: 9
        ( C ) IDENTIFICATION METHOD: by experiment
        ( D ) OTHER INFORMATION: /label=Xaa
            / note= "L-aspartic acid beta-t-butyl ester"

( i x ) FEATURE:
        ( A ) NAME/KEY: Modified-site
        ( B ) LOCATION: 10
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:45:

```
Xaa  Asn  Trp  His  Gly  Thr  Ala  Pro  Xaa  Xaa
1                   5                        10
```

( 2 ) INFORMATION FOR SEQ ID NO:46:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            " Nalpha-9-fluorenylmethyloxycarbonyl-L-valine"

( x i ) SEQUENCE DESCRIPTION: SEQ ID NO:46:

```
Xaa  Tyr  Phe  Ala  His  Leu  Thr  Leu  Ile
1                   5
```

( 2 ) INFORMATION FOR SEQ ID NO:47:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            " Nalpha-9-fluorenylmethyloxycarbonyl-L-valine"

( i x ) FEATURE:
        ( A ) NAME/KEY: Modified-site
        ( B ) LOCATION: 8
        ( C ) IDENTIFICATION METHOD: by experiment
        ( D ) OTHER INFORMATION: /label=Xaa
            / note= "beta-(2-thienyl)-L-alanine"

( x i ) SEQUENCE DESCRIPTION: SEQ ID NO:47:

```
Xaa  Tyr  Phe  Ala  His  Leu  Thr  Xaa  Ile
1                   5
```

( 2 ) INFORMATION FOR SEQ ID NO:48:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 10
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:48:

```
Val  Tyr  Phe  Ala  His  Leu  Thr  Leu  Ile  Xaa
1                  5                        10
```

( 2 ) INFORMATION FOR SEQ ID NO:49:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 8
        ( C ) IDENTIFICATION METHOD: by experiment
        ( D ) OTHER INFORMATION: /label=Xaa
            / note= "beta-(2-thienyl)-L-alanine"

( i x ) FEATURE:
        ( A ) NAME/KEY: Modified-site
        ( B ) LOCATION: 10
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:49:

```
Val  Tyr  Phe  Ala  His  Leu  Thr  Xaa  Ile  Xaa
1                  5                        10
```

( 2 ) INFORMATION FOR SEQ ID NO:50:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            " Nalpha-9-fluorenylmethyloxycarbonylglycine"

( x i ) SEQUENCE DESCRIPTION: SEQ ID NO:50:

```
Xaa  Phe  Ile  Gly  Trp  Gly  Asn
1                  5
```

( 2 ) INFORMATION FOR SEQ ID NO:51:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 9
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:51:

```
Gly  Phe  Ile  Gly  Trp  Gly  Asn  Asp  Xaa
1                  5
```

( 2 ) INFORMATION FOR SEQ ID NO:52:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            " Nalpha-9-fluorenylmethyloxycarbonylglycine"

( i x ) FEATURE:
        ( A ) NAME/KEY: Modified-site
        ( B ) LOCATION: 8
        ( C ) IDENTIFICATION METHOD: by experiment
        ( D ) OTHER INFORMATION: /label=Xaa
            / note= "L-aspartic acid beta-t-butyl ester"

( i x ) FEATURE:
        ( A ) NAME/KEY: Modified-site
        ( B ) LOCATION: 9
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:52:

```
Xaa  Phe  Ile  Gly  Trp  Gly  Asn  Xaa  Xaa
 1                    5
```

( 2 ) INFORMATION FOR SEQ ID NO:53:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            " Nalpha-9-fluorenylmethyloxycarbonylglycine"

( x i ) SEQUENCE DESCRIPTION: SEQ ID NO:53:

```
Xaa  Tyr  Pro  Trp  Trp  Asn  Tyr  Arg
 1                    5
```

( 2 ) INFORMATION FOR SEQ ID NO:54:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 10
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:54:

Gly Tyr Pro Trp Trp Asn Tyr Arg Asp Xaa
1               5                       10

( 2 ) INFORMATION FOR SEQ ID NO:55:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            "Nalpha-9-fluorenylmethyloxycarbonylglycine"

( i x ) FEATURE:
        ( A ) NAME/KEY: Modified-site
        ( B ) LOCATION: 9
        ( C ) IDENTIFICATION METHOD: by experiment
        ( D ) OTHER INFORMATION: /label=Xaa
            / note= "L-aspartic acid beta-t-butyl ester"

( i x ) FEATURE:
        ( A ) NAME/KEY: Modified-site
        ( B ) LOCATION: 10
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:55:

Xaa Tyr Pro Trp Trp Asn Tyr Arg Xaa Xaa
1               5                       10

( 2 ) INFORMATION FOR SEQ ID NO:56:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
            "Nalpha-9-fluorenylmethyloxycarbonylglycine"

( x i ) SEQUENCE DESCRIPTION: SEQ ID NO:56:

Xaa Ser Ala Ala Val Tyr Phe
1               5

( 2 ) INFORMATION FOR SEQ ID NO:57:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

(A) NAME/KEY: Modified-site
            (B) LOCATION: 9
            (C) IDENTIFICATION METHOD: by experiment
            (D) OTHER INFORMATION: /label=Xaa
                    / note= "L-tryptophan benzyl ester"

(xi) SEQUENCE DESCRIPTION: SEQ ID NO:57:

Gly  Ser  Ala  Ala  Val  Tyr  Phe  Asp  Xaa
    1                   5

(2) INFORMATION FOR SEQ ID NO:58:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (C) IDENTIFICATION METHOD: by experiment
            (D) OTHER INFORMATION: /label=Xaa
                    / note=
                    "Nalpha-9-fluorenylmethyloxycarbonylglycine"

(ix) FEATURE:
            (A) NAME/KEY: Modified-site
            (B) LOCATION: 8
            (C) IDENTIFICATION METHOD: by experiment
            (D) OTHER INFORMATION: /label=Xaa
                    / note= "L-aspartic acid beta-t-butyl ester"

(ix) FEATURE:
            (A) NAME/KEY: Modified-site
            (B) LOCATION: 9
            (C) IDENTIFICATION METHOD: by experiment
            (D) OTHER INFORMATION: /label=Xaa
                    / note= "L-tryptophan benzyl ester"

(xi) SEQUENCE DESCRIPTION: SEQ ID NO:58:

Xaa  Ser  Ala  Ala  Val  Tyr  Phe  Xaa  Xaa
    1                   5

(2) INFORMATION FOR SEQ ID NO:59:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:59:

Gly  Phe  Ile  Gly  Trp  Gly  Asn  Asp  Trp  Val  Tyr  Phe  Ala  His  Leu  Asp
    1                   5                       10                      15

Ile  Ile  Trp (2) INFORMATION FOR SEQ ID NO:60:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:60:

Gly Ser Ala Ala Val Tyr Phe Asp Trp Val Tyr Phe Ala His Leu Asp
1               5                       10                      15

Ile Ile Trp ( 2 ) INFORMATION FOR SEQ ID NO:61:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 7
        ( C ) IDENTIFICATION METHOD: by experiment
        ( D ) OTHER INFORMATION: /label=Xaa
            / note= "L-aspartic acid beta-benzyl ester"

( i x ) FEATURE:
        ( A ) NAME/KEY: Modified-site
        ( B ) LOCATION: 10
        ( C ) IDENTIFICATION METHOD: by experiment
        ( D ) OTHER INFORMATION: /label=Xaa
            / note= "L-tryptophan benzyl ester"

( x i ) SEQUENCE DESCRIPTION: SEQ ID NO:61:

Val Tyr Phe Ala His Leu Xaa Ile Ile Xaa
1               5                   10

( 2 ) INFORMATION FOR SEQ ID NO:62:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note=
              " Nalpha-9-fluorenylmethyloxycarbonyl-L-valine"

( i x ) FEATURE:
        ( A ) NAME/KEY: Modified-site
        ( B ) LOCATION: 7
        ( C ) IDENTIFICATION METHOD: by experiment
        ( D ) OTHER INFORMATION: /label=Xaa
            / note= "L-aspartic acid beta-benzyl ester"

( x i ) SEQUENCE DESCRIPTION: SEQ ID NO:62:

Xaa Tyr Phe Ala His Leu Xaa Ile Ile
1               5

( 2 ) INFORMATION FOR SEQ ID NO:63:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:63:

Val Tyr Phe Ser His Leu Asp Ile Ile Trp (2) INFORMATION FOR SEQ ID NO:64:

(i) SEQUENCE CHARACTERISTICS:
        (A) LENGTH: 20
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (C) IDENTIFICATION METHOD: by experiment
        (D) OTHER INFORMATION: /label=Xaa
            / note= "H, X1-Gly, X2-,X3-Cys, or X2-thioethyl-
            ketone; X1= X3= H, benzyloxycarbonyl, t-butyloxy-
            carbonyl, 9- fluorenylmethyloxycarbonyl, carboxylower-
            alkanoyl or lower alkanoyl, X2= H or acetamidomethyl"

(ix) FEATURE:
        (A) NAME/KEY: Modified-site
        (B) LOCATION: 2
        (C) IDENTIFICATION METHOD: by experiment
        (D) OTHER INFORMATION: /label=Xaa
            / note= "Asn, Asp, Phe, Tyr,
            Ser or a single bond"

(ix) FEATURE:
        (A) NAME/KEY: Modified-site
        (B) LOCATION: 3
        (C) IDENTIFICATION METHOD: by experiment
        (D) OTHER INFORMATION: /label=Xaa
            / note= "Trp, Ile, Pro, Ala,
            or a single bond"

(ix) FEATURE:
        (A) NAME/KEY: Modified-site
        (B) LOCATION: 4
        (C) IDENTIFICATION METHOD: by experiment
        (D) OTHER INFORMATION: /label=Xaa
            / note= "His, Lys, Gly, Trp,
            Ala, or a single bond"

(ix) FEATURE:
        (A) NAME/KEY: Modified-site
        (B) LOCATION: 5
        (C) IDENTIFICATION METHOD: by experiment
        (D) OTHER INFORMATION: /label=Xaa
            / note= "Gly, Thr, Trp, Val,
            or a single bond"

(ix) FEATURE:
        (A) NAME/KEY: Modified-site
        (B) LOCATION: 6
        (C) IDENTIFICATION METHOD: by experiment
        (D) OTHER INFORMATION: /label=Xaa
            / note= "Gly, Thr, Asn, Tyr,
            Asp or a single bond"

(ix) FEATURE:
        (A) NAME/KEY: Modified-site
        (B) LOCATION: 7
        (C) IDENTIFICATION METHOD: by experiment
        (D) OTHER INFORMATION: /label=Xaa
            / note= "Ala, Ser, Asn, Asp, Tyr, Phe,
            or a single bond"

(ix) FEATURE:
        (A) NAME/KEY: Modified-site
        (B) LOCATION: 8
        (C) IDENTIFICATION METHOD: by experiment
        (D) OTHER INFORMATION: /label=Xaa
            / note= "Pro, Ala, Arg, or
            a single bond"

(ix) FEATURE:

(A) NAME/KEY: Modified-site
(B) LOCATION: 9
(C) IDENTIFICATION METHOD: by experiment
(D) OTHER INFORMATION: /label=Xaa
/ note= "Y1-Asp, Y2-Cys, or a single
bond, and Y1= hydroxy or lower alkoxy,
and Y2=hydrogen"

(ix) FEATURE:
(A) NAME/KEY: Modified-site
(B) LOCATION: 10
(C) IDENTIFICATION METHOD: by experiment
(D) OTHER INFORMATION: /label=Xaa
/ note= "Trp or Ala"

(ix) FEATURE:
(A) NAME/KEY: Modified-site
(B) LOCATION: 11
(C) IDENTIFICATION METHOD: by experiment
(D) OTHER INFORMATION: /label=Xaa
/ note= "Val, Pro, or a single bond"

(ix) FEATURE:
(A) NAME/KEY: Modified-site
(B) LOCATION: 12
(C) IDENTIFICATION METHOD: by experiment
(D) OTHER INFORMATION: /label=Xaa
/ note= "Tyr"or a single bond"

(ix) FEATURE:
(A) NAME/KEY: Modified-site
(B) LOCATION: 14
(C) IDENTIFICATION METHOD: by experiment
(D) OTHER INFORMATION: /label=Xaa
/ note= "Ala, N-methyl-Ala, Ser,
or Cys"

(ix) FEATURE:
(A) NAME/KEY: Modified-site
(B) LOCATION: 15
(C) IDENTIFICATION METHOD: by experiment
(D) OTHER INFORMATION: /label=Xaa
/ note= "His or Trp"

(ix) FEATURE:
(A) NAME/KEY: Modified-site
(B) LOCATION: 16
(C) IDENTIFICATION METHOD: by experiment
(D) OTHER INFORMATION: /label=Xaa
/ note= "Leu or norvaline"

(ix) FEATURE:
(A) NAME/KEY: Modified-site
(B) LOCATION: 17
(C) IDENTIFICATION METHOD: by experiment
(D) OTHER INFORMATION: /label=Xaa
/ note= "Asp, Thr, Asn, Ser, Gly,
or Glu"

(ix) FEATURE:
(A) NAME/KEY: Modified-site
(B) LOCATION: 18
(C) IDENTIFICATION METHOD: by experiment
(D) OTHER INFORMATION: /label=Xaa
/ note= "Ile, Leu, beta-cyclohexyl-Ala,
2- aminobutanoic acid, beta-(2-thienyl)-Ala,
Met, Tyr, N- methylleucine, N-methyl-
isoleucine, phenyl-Gly or norleucine"

(ix) FEATURE:
(A) NAME/KEY: Modified-site
(B) LOCATION: 20
(C) IDENTIFICATION METHOD: by experiment
(D) OTHER INFORMATION: /label=Xaa
/ note= "Trp-Z, Phe-Z, or Tyr-Z,
and Z=hydroxy, lower alkoxy or amino"

(xi) SEQUENCE DESCRIPTION: SEQ ID NO:64:

Xaa Xaa Xaa Xaa Xaa Xaa Xaa Xaa Xaa Xaa Xaa Xaa Phe Xaa Xaa Xaa

|   | 1 |   |   | 5 |   |   |   | 10 |   |   | 15 |
|---|---|---|---|---|---|---|---|---|---|---|---|

Xaa Xaa Ile Xaa
         20

( 2 ) INFORMATION FOR SEQ ID NO:65:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
            / note= "H, X1-Gly, X2-,X3-Cys, or X2-thioethyl-
            ketone; X1= X3= H, benzyloxycarbonyl, t-butyloxy-
            carbonyl, 9- fluorenylmethyloxycarbonyl, carboxylower-
            alkanoyl or lower alkanoyl, X2= H or acetamidomethyl"

( i x ) FEATURE:
        ( A ) NAME/KEY: Modified-site
        ( B ) LOCATION: 2
        ( C ) IDENTIFICATION METHOD: by experiment
        ( D ) OTHER INFORMATION: /label=Xaa
            / note= "Asn, Asp, Phe, Tyr, Ser, or
            a single bond"

( i x ) FEATURE:
        ( A ) NAME/KEY: Modified-site
        ( B ) LOCATION: 3
        ( C ) IDENTIFICATION METHOD: by experiment
        ( D ) OTHER INFORMATION: /label=Xaa
            / note= "Trp, Ile, Pro, Ala,
            or a single bond"

( i x ) FEATURE:
        ( A ) NAME/KEY: Modified-site
        ( B ) LOCATION: 4
        ( C ) IDENTIFICATION METHOD: by experiment
        ( D ) OTHER INFORMATION: /label=Xaa
            / note= "His, Lys, Gly, Trp, Ala,
            or a single bond"

( i x ) FEATURE:
        ( A ) NAME/KEY: Modified-site
        ( B ) LOCATION: 5
        ( C ) IDENTIFICATION METHOD: by experiment
        ( D ) OTHER INFORMATION: /label=Xaa
            / note= "Gly, Thr, Trp, Val,
            or a single bond"

( i x ) FEATURE:
        ( A ) NAME/KEY: Modified-site
        ( B ) LOCATION: 6
        ( C ) IDENTIFICATION METHOD: by experiment
        ( D ) OTHER INFORMATION: /label=Xaa
            / note= "Gly, Thr, Asn, Tyr, Asp,
            or a single bond"

( i x ) FEATURE:
        ( A ) NAME/KEY: Modified-site
        ( B ) LOCATION: 7
        ( C ) IDENTIFICATION METHOD: by experiment
        ( D ) OTHER INFORMATION: /label=Xaa
            / note= "Ala, Ser, Asn, Asp, Tyr, Phe,
            or a single bond"

( i x ) FEATURE:
        ( A ) NAME/KEY: Modified-site
        ( B ) LOCATION: 8
        ( C ) IDENTIFICATION METHOD: by experiment
        ( D ) OTHER INFORMATION: /label=Xaa
            / note= "Pro, Ala, Arg, or (ix) FEATURE:
    (A) NAME/KEY: Modified-site
    (B) LOCATION: 9
    (C) IDENTIFICATION METHOD: by experiment
    (D) OTHER INFORMATION: /label=Xaa
        /note= "Y1-Asp, Y2-Cys, or a single
        bond, and Y1= hydroxy or alkoxy and
        Y2=hydrogen"

(ix) FEATURE:
    (A) NAME/KEY: Modified-site
    (B) LOCATION: 17
    (C) IDENTIFICATION METHOD: by experiment
    (D) OTHER INFORMATION: /label=Xaa
        /note= "Asp, Thr, Asn, Ser, Gly or Glu"

(ix) FEATURE:
    (A) NAME/KEY: Modified-site
    (B) LOCATION: 18
    (C) IDENTIFICATION METHOD: by experiment
    (D) OTHER INFORMATION: /label=Xaa
        /note= "Ile, Leu, beta-cyclohexyl-Ala,
        2- aminobutanoic acid, beta-(2-thienyl)-Ala,
        Met, Tyr, N- methyl-Leu, N-methyl-Ile,
        phenyl-Gly or norleucine"

(xi) SEQUENCE DESCRIPTION: SEQ ID NO:65:

```
Xaa Xaa Xaa Xaa Xaa Xaa Xaa Xaa Xaa Trp Val Tyr Phe Ala His Leu
 1               5                  10                  15
Xaa Xaa Ile Trp
         20
```

(2) INFORMATION FOR SEQ ID NO:66:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (C) IDENTIFICATION METHOD: by experiment
        (D) OTHER INFORMATION: /label=Xaa
            /note= "H, X1-Gly, X2-,X3-Cys, or X2-thioethyl-
            ketone; X1= X3= H, benzyloxycarbonyl, t-butyloxy-
            carbonyl, 9- fluorenylmethyloxycarbonyl, carboxylower-
            alkanoyl or lower alkanoyl, X2= H or acetamidomethyl"

(ix) FEATURE:
        (A) NAME/KEY: Modified-site
        (B) LOCATION: 9
        (C) IDENTIFICATION METHOD: by experiment
        (D) OTHER INFORMATION: /label=Xaa
            /note= "Y1-Asp, and Y1= a single
            bond, hydroxy or lower alkoxy"

(ix) FEATURE:
        (A) NAME/KEY: Modified-site
        (B) LOCATION: 17
        (C) IDENTIFICATION METHOD: by experiment
        (D) OTHER INFORMATION: /label=Xaa
            /note= "Asp, Thr, Asn, Ser, Gly, or Glu"

(ix) FEATURE:
        (A) NAME/KEY: Modified-site
        (B) LOCATION: 18
        (C) IDENTIFICATION METHOD: by experiment
        (D) OTHER INFORMATION: /label=Xaa
            /note= "Ile, Leu, beta-cyclohexyl-Ala,
            2- aminobutanoic acid, beta-(2-thienyl)-Ala,
            Met, Tyr, N- methyl-Leu, N-methyl-Ile, phenyl-Gly or norleucine"

( x i ) SEQUENCE DESCRIPTION: SEQ ID NO:66:

```
Xaa Asn Trp His Gly Thr Ala Pro Xaa Trp Val Tyr Phe Ala His Leu
1               5                   10                  15
Xaa Xaa Ile Trp
            20
```

( 2 ) INFORMATION FOR SEQ ID NO:67:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Disulfide-bond
        ( B ) LOCATION: 1..9
        ( C ) IDENTIFICATION METHOD: by experiment ( i x ) FEATURE:
        ( A ) NAME/KEY: Modified-site
        ( B ) LOCATION: 17
        ( C ) IDENTIFICATION METHOD: by experiment
        ( D ) OTHER INFORMATION: /label=Xaa
            / note= "Asp, Thr, Asn, Ser,
            Gly, or Glu"

( i x ) FEATURE:
        ( A ) NAME/KEY: Modified-site
        ( B ) LOCATION: 18
        ( C ) IDENTIFICATION METHOD: by experiment
        ( D ) OTHER INFORMATION: /label=Xaa
            / note= "Ile, Leu, beta-cyclohexyl-Ala,
            2- aminobutanoic acid, beta-(2-thienyl)-Ala,
            Met, Tyr, N- methyl-Leu, N-methyl-Ile,
            phenyl-Gly, or norleucine"

( x i ) SEQUENCE DESCRIPTION: SEQ ID NO:67:

```
Cys Asn Trp His Gly Thr Ala Pro Cys Trp Val Tyr Phe Ala His Leu
1               5                   10                  15
Xaa Xaa Ile Trp
            20
```

( 2 ) INFORMATION FOR SEQ ID NO:68:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..9
        ( C ) IDENTIFICATION METHOD: by experiment
        ( D ) OTHER INFORMATION: /label=Gly..Asp
            / note= "bond between amino acids 1 and 9"

( x i ) SEQUENCE DESCRIPTION: SEQ ID NO:68:

```
Gly Asn Trp His Gly Thr Ala Pro Asp Trp Val Tyr Phe Ala His Leu
1               5                   10                  15
Thr Leu Ile Trp
            20
```

( 2 ) INFORMATION FOR SEQ ID NO:69:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1..9
    ( C ) IDENTIFICATION METHOD: by experiment
    ( D ) OTHER INFORMATION: /label=Gly..Asp
        / note= "bond between amino acids 1 and 9"

( i x ) FEATURE:
    ( A ) NAME/KEY: Modified-site
    ( B ) LOCATION: 18
    ( C ) IDENTIFICATION METHOD: by experiment
    ( D ) OTHER INFORMATION: /label=Xaa
        / note= "beta-(2-thienyl)-L-alanine"

( x i ) SEQUENCE DESCRIPTION: SEQ ID NO:69:

```
Gly  Asn  Trp  His  Gly  Thr  Ala  Pro  Asp  Trp  Val  Tyr  Phe  Ala  His  Leu
1                  5                           10                          15

Thr  Xaa  Ile  Trp
              20
```

( 2 ) INFORMATION FOR SEQ ID NO:70:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( C ) IDENTIFICATION METHOD: by experiment
    ( D ) OTHER INFORMATION: /label=Asn
        / note= "thioethylketone-asparagine"

( i x ) FEATURE:
    ( A ) NAME/KEY: Modified-site
    ( B ) LOCATION: 1..8
    ( C ) IDENTIFICATION METHOD: by experiment
    ( D ) OTHER INFORMATION: /label=Asn..Cys
        / note= "bond between S group of thioethyl-
        ketone- asparagine at position 1 and Cys at
        position 8"

( x i ) SEQUENCE DESCRIPTION: SEQ ID NO:70:

```
Asn  Trp  His  Gly  Thr  Ala  Pro  Cys  Trp  Val  Tyr  Phe  Ala  His  Leu  Ser
1                  5                           10                          15

Met  Ile  Trp
```

( 2 ) INFORMATION FOR SEQ ID NO:71:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1..8
    ( C ) IDENTIFICATION METHOD: by experiment ( D ) OTHER INFORMATION: /label=Gly..Asp
/ note= "bond between amino acids 1 and 8"

( x i ) SEQUENCE DESCRIPTION: SEQ ID NO:71:

Gly Phe Ile Gly Trp Gly Asn Asp Trp Val Tyr Phe Ala His Leu Asp
1               5                   10                  15

Ile Ile Trp ( 2 ) INFORMATION FOR SEQ ID NO:72:

( i ) SEQUENCE CHARACTERISTICS:
 ( A ) LENGTH: 20 amino acids
 ( B ) TYPE: amino acid
 ( C ) STRANDEDNESS: single
 ( D ) TOPOLOGY: linear ( i i ) MOLECULE TYPE: peptide ( i x ) FEATURE:
 ( A ) NAME/KEY: Modified-site
 ( B ) LOCATION: 1..9
 ( C ) IDENTIFICATION METHOD: by experiment
 ( D ) OTHER INFORMATION: /label=Gly..Asp
  / note= "bond between amino acids 1 and 9"

( x i ) SEQUENCE DESCRIPTION: SEQ ID NO:72:

Gly Tyr Pro Trp Trp Asn Tyr Arg Asp Trp Val Tyr Phe Ala His Leu
1               5                   10                  15

Asp Ile Ile Trp ( 2 ) INFORMATION FOR SEQ ID NO:73:

( i ) SEQUENCE CHARACTERISTICS:
 ( A ) LENGTH: 19 amino acids
 ( B ) TYPE: amino acid
 ( C ) STRANDEDNESS: single
 ( D ) TOPOLOGY: linear ( i i ) MOLECULE TYPE: peptide ( i x ) FEATURE:
 ( A ) NAME/KEY: Modified-site
 ( B ) LOCATION: 1..8
 ( C ) IDENTIFICATION METHOD: by experiment
 ( D ) OTHER INFORMATION: /label=Gly..Asp
  / note= "bond between amino acids 1 and 8"

( x i ) SEQUENCE DESCRIPTION: SEQ ID NO:73:

Gly Ser Ala Ala Val Tyr Phe Asp Trp Val Tyr Phe Ala His Leu Asp
1               5                   10                  15

Ile Ile Trp ( 2 ) INFORMATION FOR SEQ ID NO:74:

( i ) SEQUENCE CHARACTERISTICS:
 ( A ) LENGTH: 10 amino acids
 ( B ) TYPE: amino acid
 ( C ) STRANDEDNESS: single
 ( D ) TOPOLOGY: linear ( i i ) MOLECULE TYPE: peptide ( i x ) FEATURE:
 ( A ) NAME/KEY: Modified-site
 ( B ) LOCATION: 1..9
 ( C ) IDENTIFICATION METHOD: by experiment
 ( D ) OTHER INFORMATION: /label=Gly..Asp
  / note= "bond between amino acids 1 and 9"

( x i ) SEQUENCE DESCRIPTION: SEQ ID NO:74:

```
Gly  Tyr  Pro  Trp  Trp  Asn  Tyr  Arg  Asp  Trp
1                  5                        10
```

( 2 ) INFORMATION FOR SEQ ID NO:75:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 1..8
      ( C ) IDENTIFICATION METHOD: by experiment
      ( D ) OTHER INFORMATION: /label=Gly..Asp
         / note= "bond between amino acids 1 and 8"

( x i ) SEQUENCE DESCRIPTION: SEQ ID NO:75:

```
Gly  Ser  Ala  Ala  Val  Tyr  Phe  Asp  Trp
1                  5
```

( 2 ) INFORMATION FOR SEQ ID NO:76:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Modified-site
      ( B ) LOCATION: 1..9
      ( C ) IDENTIFICATION METHOD: by experiment
      ( D ) OTHER INFORMATION: /label=Gly..Asp
         / note= "bond between amino acids 1 and 9"

( x i ) SEQUENCE DESCRIPTION: SEQ ID NO:76:

```
Gly  Asn  Trp  His  Gly  Thr  Ala  Pro  Asp  Trp
1                  5                        10
```

ENDOTHELIN-ANTAGONIZING PEPTIDE

This application is a 371 of PCT/JP94/01011 filed Jun. 23, 1994.

TECHNICAL FIELD

The present invention relates to a novel peptide which has endothelin-antagonizing activity. The peptide has excellent endothelin-antagonizing activity, and is therefore useful for treatment of hypertension, asthma, cerebral apoplexy, angina pectoris, actute renal insufficiency, cardiac infarction, cerebral vasospasm, etc.

BACKGROUND ART

Endothelin is a cyclic peptide which possesses a strong, long-lasting vasoconstricting effect, and is thought to be one of the substances responsible for hypertension, asthma, cerebral apoplexy, angina pectoris, actute renal insufficiency, cardiac infarction, and cerebral vasospasm. Consequently, a substance which antagonizes endothelin and inhibits its effects is expected to be useful for the treatment and prevention of these diseases.

It is known that the cyclic peptide represented by the following formula (A) exhibits the endothelin antagonism (Japanese Published Unexamined Patent Application No. 130299/91):

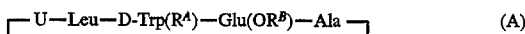

(A)

(wherein U represents D-Val or D-allo-Ile, $R^A$ represents hydrogen or an amino-protective group, and $R^B$ represents hydrogen or a carboxy-protective group). Related cyclic peptides BE-18257 derivatives and BQ-123 derivatives have also been reported (Japanese Published Unexamined Patent Application No. 94692/91, U.S. Pat. No. 5,114,918).

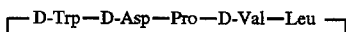

(BQ-123)

Cyclodepsipeptides represented by the following formula have been reported as cyclic peptides containing abnormal amino acid [Cochinmicins; J. Antibiotics, 45, 1709-1722 (1992)].

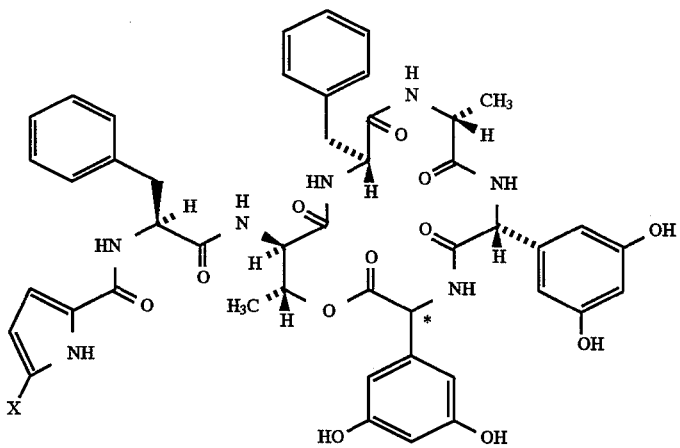

| Cochinmicin | X | * |
|---|---|---|
| 1 | I | H | R |
| 2 | II | Cl | S |
| 3 | III | Cl | R |

Olygopeptides represented by the following formula have also been reported as other peptides having the endothelin-antagonizing activity [EP-A-0457195, J. Pharm. Exp. Ther., 264, 1040–1046 (1992)].

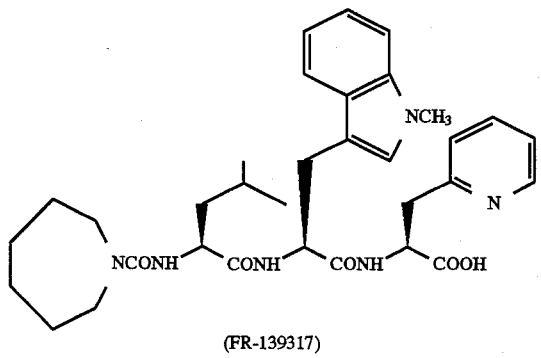

(FR-139317)

The similar peptides represented by the following formula have further been reported (Abstract of the 65th Conference of Biochemical Society of Japan, p 769)

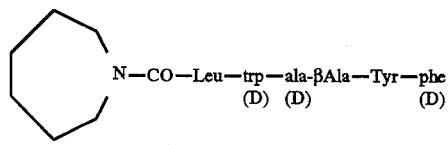

There have been many reports on endothelin derivatives and partial peptides of endothelin [WO91-13089, Japanese Published Unexamined Patent Application No. 59098/93, WO 92-02237, J. Med. Chem., 35, 3301–3303 (1992), Biochem. Biophys. Res. Commun., 179, 286–292 (1991), Biochem. Biophys. Res. Commun., 184, 953–959 (1992), FEBS Lett., 311, 12–16 (1992), Biochem. Biophys. Res. Commun., 184, 100–106 (1992), Biochem. Biophys. Res. Commun., 183, 566–571 (1992), Proc. Natl. Acad. Sci. U.S.A., 88, 7443–7446 (1991), J. Pharm. Exp. Ther., 260, 632–636 (1992), EP-A-499266, etc].

There have also been reports on random modification of C-terminal peptides of endothelin-1 [BioMed. Chem. Lett., 3. 497–502 (1993), BioMed. Chem. Lett., 3, 519–524 (1993)].

DISCLOSURE OF THE INVENTION

According to the present invention, there is provided a peptide compound represented by the following formula (I):

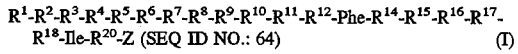

{wherein $R^1$ represents

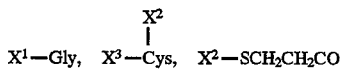

or hydrogen;
$R^2$ represents Asn, Asp, Phe, Tyr, Ser, or a single bond;
$R^3$ represents Trp, Ile, Pro, Ala, or a single bond;
$R^4$ represents His, Lys, Gly, Trp, Ala, or a single bond;
$R^5$ represents Gly, Thr, Trp, Val, or a single bond;
$R^6$ represents Gly, Thr, Asn, Tyr, Asp, or a single bond;
$R^7$ represents Ala, Ser, Asn, Asp, Tyr, Phe, or a single bond;
$R^8$ represents Pro, Ala, Arg, or a single bond;
$R^9$ represents

or a single bond;
$R^{10}$ represents Trp or Ala;
$R^{11}$ represents Val, Pro, or a single bond;
$R^{12}$ represents Tyr or a single bond;
$R^{14}$ represents Ala, MeAla, Ser, or Cys;
$R^{15}$ represents His or Trp;
$R^{16}$ represents Leu or Nva;
$R^{17}$ represents Asp, Thr, Asn, Ser, Gly, or Glu;
$R^{18}$ represents Ile, Leu, Cha, Abu, Thi, Met, Tyr, MeLeu, MeIle, Phg, or Nle;
$R^{20}$ represents Trp, Phe, or Tyr; and
Z represents hydroxy, lower alkoxy, or amino
(wherein $X^1$ and $X^3$ each represent hydrogen, benzyloxycarbonyl, t-butyloxycarbonyl, 9-fluorenylmethyloxycarbonyl, or carboxy-substituted or unsubstituted lower alkanoyl; $X^2$ represents hydrogen or acetamidomethyl; $Y^1$ represents hydroxy or lower alkoxy; $Y^2$ represents hydrogen; or $X^1$ and $Y^1$ or $X^2$ and $Y^2$ are combined together to form a single bond as $X^1$-$Y^1$ or $X^2$-$Y^2$; and Nva represents a norvaline residue, Cha represents a β-cyclohexylalanine residue, Abu represents a 2-aminobutanoic acid residue, Thi represents a β-(2-thienyl) alanine residue, Phg represents a phenylglycine residue, Nle represents a norleucine residue, MeAla represents a N-methylalanine residue, MeLeu represents a N-methylleucine residue, MeIle represents a N-methylisoleucine residue, and amino acid residues other than Gly each represent a D-, L-, or DL-amino acid residue)}, or a pharmaceutically acceptable salt thereof.

The peptide compound represented by the above formula (I) is hereinafter referred to as Compound (I), and the same applies to the compounds of other formula numbers.

In the definitions for the above formula (I), the alkyl moiety of lower alkoxy means a straight-chain or branched alkyl group having 1 to 6 carbon atoms such as methyl, ethyl, propyl, isopropyl, butyl, isobutyl, sec-butyl, tert-butyl, pentyl, neopentyl, hexyl, and isohexyl. The lower alkanoyl means a straight-chain or branched alkanoyl group having 1 to 6 carbon atoms such as formyl, acetyl, propionyl, butyryl, valeryl, pivaloyl, and pentanoyl.

The above-mentioned pharmaceutically acceptable salts of Compound (I) include pharmaceutically acceptable acid addition salts, metal salts, and organic base addition salts. Examples of the pharmaceutically acceptable acid addition salts are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminum salts, and zinc salts. Examples of the pharmaceutically acceptable organic base addition salts are salts with primary amines such as methylamine, ethylamine, and aniline, secondary amines such as dimethylamine, diethylamine, pyrrolidine, piperidine, morpholine, and piperazine, and tertiary amines such as trimethylamine, triethylamine, N,N-dimethylaniline, and pyridine, and ammonium salts.

The present invention is described in detail below.

The abbreviations for the amino acids and their protective groups used in this specification follow the recommendations of the IUPAC-IUB Commission relating to biochemical nomenclature [Biochemistry, 11, 1726, (1972)].

Unless otherwise provided, the abbreviations below indicate the corresponding amino acids and protective groups as follows.

Gly: glycine
Ala: L-alanine
D-Ala: D-alanine
Thr: L-threonine
Pro: L-proline
Asp: L-aspartic acid
Asn: L-asparagine
Asx: L-aspartic acid or L-asparagine
His: L-histidine
Phe: L-phenylalanine
D-Phe: D-phenylalanine
Tyr: L-tyrosine
Trp: L-tryptophan
D-Trp: D-tryptophan
Val: L-valine
Ile: L-isoleucine
D-Ile: D-isoleucine
Leu: L-leucine
Glu: L-glutamic acid
Glx: L-glutamic acid or L-glutamine
Lys: L-lysine
Ser: L-serine
Met: L-methionine
Cys: L-cysteine
Thi: β-(2-thienyl)-L-alanine
Cha: β-cyclohexyl-L-alanine
Abu: L-2-aminobutanoic acid
MeAla: N-methyl-L-alanine
MeLeu: N-methyl-L-leucine
MeIle: N-methyl-L-isoleucine
Phg: L-phenylglycine
Nle: L-norleucine
Nva: L-norvaline
Mpa: β-mercaptopropionic acid
Acm: acetamidomethyl
Fmoc: 9-fluorenylmethyloxycarbonyl
Boc: t-butyloxycarbonyl t-Bu: t-butyl
Trt: trityl
Bzl: benzyl
CHO: formyl
Bom: benzyloxymethyl
Pmc: 2,2,5,7,8-pentamethylchromane-6-sulfonyl
Suc: succinyl The abbreviations below indicate the corresponding side-chain-protected amino acids as follows. Fmoc-Asp(To-Bu)-OH:

β-t-butyl $N^\alpha$-9-fluorenylmethyloxycarbonyl-L-aspartate Fmoc-Asp(OBzl)-OH:

β-benzyl $N^\alpha$-9-fluorenylmethyloxycarbonyl-L-aspartate Fmoc-His(Trt)-OH:

$N^\alpha$-9-fluorenylmethyloxycarbonyl-$N^{im}$-trityl-L-histidine Fmoc-Tyr(t-Bu)-OH:

$N^\alpha$-9-fluorenylmethyloxycarbonyl-O-t-butyl-L-tyrosine Fmoc-Thr(t-Bu)-OH:

$N^\alpha$-9-fluorenylmethyloxycarbonyl-O-t-butyl-L-threonine Fmoc-Ser (t-Bu)-OH:

$N^\alpha$-9-fluorenylmethyloxycarbonyl-O-t-butyl-L-serine Fmoc-Asn(Trt)-OH:

$N^\alpha$-9-fluorenylmethyloxycarbonyl-$N^\gamma$-trityl-L-asparagine Fmoc-Arg(Pmc)-OH:

$N^\alpha$-9-fluorenylmethyloxycarbonyl-$N^g$-2,2,5,7,8-pentamethylchromane-6-sulfonyl-L-arginine Fmoc-Lys(Boc)-OH:

$N^\alpha$-9-fluorenylmethyloxycarbonyl-$N^\epsilon$-t-butyloxycarbonyl-L-lysine Fmoc-Cys(Trt)-OH:

$N^\alpha$-9-fluorenylmethyloxycarbonyl-S-trityl-L-cysteine Boc-Thr(Bzl)-OH:

$N^\alpha$-t-butyloxycarbonyl-O-benzyl-L-threonine Boc-His(Bom)-OH:

$N^\alpha$-t-butyloxycarbonyl-$N^{im}$-benzyloxymethyl-L-histidine Boc-Trp(CHO)-OH:

$N^\alpha$-t-butyloxycarbonyl-$N^{ind}$-formyl-L-tryptophan Boc-Ser(Bzl)-OH:

$N^\alpha$-t-butyloxycarbonyl-O-benzyl-L-serine H-Trp-OBzl: L-tryptophan benzyl ester The abbreviations below indicate the corresponding reaction solvents and reagents as follows.
PyBOP: benzotriazol-1-yloxytrispyrrolidinophosphonium-hexafluorophosphate
HOBt: N-hydroxybenzotriazole
NMM: N-methylmorpholine
DCC: dicyclohexylcarbodiimide
HONSu: N-hydroxysuccinimide
DEPC: diethylphosphorocyanidate
DNF: N,N-dimethylformamide
TFA: trifluoroacetic acid
Pd/C: palladium-carbon catalyst The processes for producing Compounds (I) are described below.

Compound (I) can be synthesized with a peptide synthesizer manufactured by Applied Biosystems, Inc., U.S.A. (ABI Co.) or manufactured by Shimazu Seisakusho, using an $N^\alpha$-t-butyloxycarbonylamino acid or an $N^\alpha$-9-fluorenyloxy-carbonylamino acid whose side chains have been appropriately protected, according to the synthesis programs of the same companies.

The cyclic peptide without S—S bonds in Compound (I) may be obtained by synthesizing a partial peptide whose side chains have been appropriately protected, with the above-described synthesizer or according to the usual liquid phase peptide synthesis method ("Fundamentals and Experiments in Peptide Synthesis", Nobuo Izumiya et al., Maruzen), obtaining a cyclized partial peptide using the above-described peptide as the starting material and a condensing agent such as PyBOP, and further condensing the obtained cyclized partial peptide with the C-terminal peptide using the peptide synthesizer, the liquid phase synthesis method, or an appropriate combination thereof.

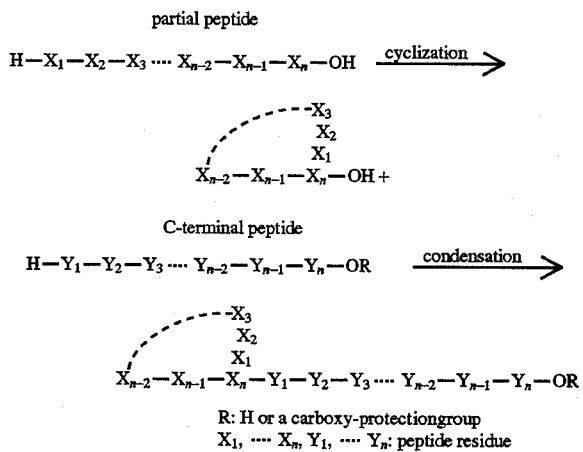

R: H or a carboxy-protectiongroup
$X_1, \cdots X_n, Y_1, \cdots Y_n$: peptide residue The cyclic peptide having a S—S bond can be obtained by oxidizing the linear peptide synthesized with the above-mentioned synthesizer in a weak alkaline aqueous solution using air or an oxidizing agent such as potassium ferricyanide.

The modified peptide having an amide bond at an N-terminal or an amino group on the side chain can be obtained by condensing carboxylic acid with the peptide synthesized with the above-mentioned synthesizer using a condensing agent (for example, PyBOP/HOBt/NMM), or condensing activated carboxylic acid such as carboxylic anhydride and carboxylic acid halide with the peptide synthesized with the above-mentioned synthesizer. Alternatively, the modified peptide having an amide bond at an N-terminal or an amino group on the side chain can also be obtained by synthesizing the peptide on the synthetic resin, performing the above-described reaction on the resin before separation of the peptide from the resin, and then separating the product.

The protected amino acid which is a starting material for Compound (I) may be obtained from ABI Co., Shimazu Seisakusho, Kokusan Chemicals, Inc., Nova Biochem Co., Watanabe Chemical, Inc., or Peptide Laboratories, Inc.

The obtained Compound (I) may be purified by high pressure liquid chromatography (referred to as HPLC hereinafter) using a C-4, C-8, or C-18 reverse phase silica gel column, column chromatography such as partition, adsorption resin, silica gel, chemically modified silica gel, reverse phase silica gel, alumina, diatomaceous earth, magnesium silicate, ion-exchange resin, and gel filtration, or thin layer chromatography.

A conventional method is used to obtain a pharmaceutically acceptable salt of Compound (I). That is, an acid addition salt or an organic base addition salt of Compound (I) can be obtained by dissolving Compound (I) in an aqueous solution of a corresponding acid or organic base, and freeze-drying the resultant solution. In addition, a metal salt of Compound (I) can be obtained by dissolving Compound (I) in an aqueous solution containing the corresponding metal ion, and purifying the solution by gel filtration or HPLC.

Examples of Compound (I) are shown in Table 1.

Compound (I) obtained in the present invention exhibits an excellent endothelin-antagonizing activity and an inhibitory effect on endothelin-1 (ET-1) contraction.

TABLE 1

| Compound No. | Sequence No. | Sequence Length | Sequence |
|---|---|---|---|
| 1 | 1 | 20 | HOOCCH₂CH₂CO—Gly—Asn—Trp—His—Gly—Thr—Ala—Pro—Asp—Trp—Val—Tyr—Phe—Ala—His—Leu—Asp—Ile—Trp—OH |
| 2 | 2 | 20 | H—Gly—Asn—Trp—His—Thr—Thr—Ala—Pro—Asp—Trp—Val—Tyr—Phe—Ala—His—Leu—Asp—Ile—Trp—OH |
| 3 | 3 | 20 | H—Gly—Asn—Trp—His—Gly—Ala—Ala—Pro—Asp—Trp—Val—Tyr—Phe—Ala—His—Leu—Asp—Ile—Trp—OH |
| 4 | 4 | 20 | H—Gly—Asn—ThrP—His—Gly—Thr—Ala—Pro—Asp—Trp—Val—Tyr—Phe—Ala—His—Leu—Asp—Ile—Trp—OH |
| 5 | 5 | 20 | H—Gly—Asp—Trp—His—Gly—Thr—Ala—Pro—Asp—Trp—Val—Tyr—Phe—Ala—His—Leu—Asp—Ile—Ile—OH |
| 6 | 6 | 20 | H—Gly—Asp—Trp—Lys—Gly—Thr—Ser—Pro—Asp—Trp—Val—Tyr—Phe—Ala—His—Leu—Asp—Ile—Ile—Phe—OH |
| 7 | 7 | 19 | H—Asn—Trp—His—Gly—Thr—Ala—Pro—Asp—Trp—Val—Tyr—Phe—Ala—His—Leu—Asp—Ile—Ile—Trp—OH |
| 8 | 8 | 18 | H—Trp—His—Gly—Thr—Ala—Pro—Asp—Trp—Val—Tyr—Phe—Ala—His—Leu—Asp—Ile—Ile—Trp—OH |
| 9 | 9 | 17 | H—His—Gly—Thr—Ala—Pro—Asp—Trp—Val—Tyr—Phe—Ala—His—Leu—Asp—Ile—Ile—Trp—OH |
| 10 | 10 | 19 | H—Gly—Asn—Trp—His—Gly—Thr—Ala—Pro—Asp—Trp—Val—Tyr—Phe—Ala—His—Leu—Asp—Ile—Ile—OH |
| 11 | 11 | 18 | H—Gly—Asn—Trp—His—Gly—Thr—Ala—Pro—Asp—Trp—Phe—Ala—His—Leu—Asp—Ile—Ile—Trp—OH |
| 12 | 12 | 11 | H—Trp—Val—Tyr—Phe—Ala—His—Leu—Asp—Ile—Ile—Trp—OH |
| 13 | 13 | 20 | H—Gly—Asn—Trp—His—Gly—Thr—Ala—Pro—Asp—Trp—Val—Tyr—Phe—Ala—His—Leu—Thr—Leu—Ile—Trp—OH |
| 14 | 14 | 20 | H—Gly—Asn—Trp—His—Gly—Thr—Ala—Pro—Asp—Trp—Val—Tyr—Phe—Ala—His—Leu—Thr—Cha—Ile—Trp—OH |
| 15 | 15 | 20 | H—Gly—Asn—Trp—His—Gly—Thr—Ala—Pro—Asp—Trp—Val—Tyr—Phe—Ala—His—Leu—Thr—Abu—Ile—Trp—OH |
| 16 | 16 | 20 | H—Gly—Asn—Trp—His—Gly—Thr—Ala—Pro—Asp—Trp—Val—Tyr—Phe—Ala—His—Leu—Asp—Leu—Ile—Trp—OH |
| 17 | 17 | 20 | H—Gly—Asn—Trp—His—Gly—Thr—Ala—Pro—Asp—Trp—Val—Tyr—Phe—Ala—His—Leu—Thr—Ile—Ile—Trp—OH |
| 18 | 18 | 20 | H—Gly—Asn—Trp—His—Gly—Thr—Ala—Pro—Asp—Trp—Val—Tyr—Phe—Ala—His—Leu—Thr—Met—Ile—Trp—OH |
| 19 | 19 | 20 | H—Gly—Asn—Trp—His—Gly—Thr—Ala—Pro—Asp—Trp—Val—Tyr—Phe—Ala—His—Leu—Thr—Tyr—Ile—Trp—OH |
| 20 | 20 | 20 | H—Gly—Asn—Trp—His—Gly—Thr—Ala—Pro—Asp—Trp—Val—Tyr—Phe—Ala—His—Leu—Asn—Tyr—Ile—Trp—OH |
| 21 | 21 | 20 | H—Gly—Asn—Trp—His—Gly—Lys—Ala—Pro—Asp—Trp—Val—Tyr—Phe—Ala—His—Leu—Ser—Met—Ile—Trp—OH |
| 22 | 22 | 20 | H—Gly—Asn—Trp—His—Gly—Lys—Ala—Pro—Asp—Trp—Val—Tyr—Phe—Ala—His—Leu—Thr—Ile—Ile—Trp—OH |
| 23 | 23 | 20 | H—Gly—Asn—Trp—His—Gly—Ser—Ala—Pro—Asp—Trp—Val—Tyr—Phe—Ala—His—Leu—Thr—MeLeu—Ile—Trp—OH |
| 24 | 24 | 20 | H—Gly—Asn—Trp—His—Gly—Thr—Ala—Pro—Asp—Trp—Val—Tyr—Phe—Ala—His—Leu—Thr—MeIle—Ile—Trp—OH |
| 25 | 25 | 20 | H—Gly—Asn—Trp—His—Gly—Thr—Ala—Pro—Asp—Trp—Val—Tyr—Phe—Ala—His—Leu—Thr—Phg—Ile—Trp—OH |
| 26 | 26 | 20 | H—Gly—Asn—Trp—His—Gly—Thr—Ala—Pro—Asp—Trp—Val—Tyr—Phe—Ala—His—Leu—Thr—Nle—Ile—Trp—OH |
| 27 | — | 20 | H—Gly—Asn—Trp—His—Gly—Thr—Ala—Pro—Asp—Trp—Val—Tyr—Phe—D-Ala—His—Leu—Thr—Thi—Ile—Trp—OH |
| 28 | — | 20 | H—Gly—Asn—Trp—His—Gly—Thr—Ala—Pro—Asp—Trp—Val—Tyr—Phe—Ala—D-Trp—Leu—Thr—Thi—Ile—Trp—OH |
| 29 | 27 | 20 | H—Gly—Asn—Trp—His—Gly—Thr—Ala—Pro—Asp—Trp—Val—Tyr—Phe—Ala—His—Nva—Thr—Thi—Ile—Trp—OH |
| 30 | 28 | 20 | H—Gly—Asn—Trp—His—Gly—Lys—Ala—Pro—Asp—Trp—Val—Tyr—Phe—Ala—His—Gly—Thr—Thi—Ile—Trp—OH |
| 31 | — | 20 | H—Gly—Asn—Trp—His—Gly—Thr—Ala—Pro—Asp—Trp—Val—Tyr—Phe—Ala—His—Leu—Thr—Thi—D-Ile—Trp—OH |
| 32 | 29 | 20 | H—Gly—Asn—Trp—His—Gly—Thr—Ala—Pro—Cys—Trp—Val—Tyr—Phe—Ala—His—Leu—Asp—Ile—Trp—OH |
| 33 | 30 | 20 | H—Cys—Asn—Trp—His—Gly—Thr—Ala—Pro—Cys—Trp—Val—Tyr—Phe—Ala—His—Leu—Asp—Ile—Trp—OH |
| 34 | 31 | 20 | H—Cys—Asn—Trp—Lys—Gly—Thr—Ser—Pro—Cys—Trp—Val—Tyr—Phe—Ala—His—Leu—Thr—Ile—Trp—OH |
| 35 | 32 | 20 | H—Cys—Asn—Trp—Lys—Gly—Thr—Ser—Pro—Cys—Trp—Val—Tyr—Phe—Ala—His—Leu—Thr—Thi—Ile—Trp—OH |
| 36 | 33 | 20 | H—Cys—Asn—Trp—His—Gly—Thr—Ala—Pro—Cys—Trp—Val—Tyr—Phe—Ala—His—Leu—Thr—Leu—Ile—Trp—OH |
| 37 | 34 | 20 | H—Cys—Asn—Trp—His—Gly—Thr—Ala—Pro—Cys—Trp—Val—Tyr—Phe—Ala—His—Leu—Thr—Ile—Ile—Trp—OH |
| 38 | 35 | 20 | H—Cys—Asn—Trp—His—Gly—Thr—Ala—Pro—Cys—Trp—Val—Tyr—Phe—Ala—His—Leu—Thr—Cha—Ile—Trp—OH |

TABLE 1-continued

| Compound No. | Sequence No. | Sequence Length | Sequence |
|---|---|---|---|
| 39 | 36 | 20 | H—Cys—Asn—Trp—His—Gly—Thr—Ala—Pro—Cys—Trp—Val—Tyr—Phe—Ala—His—Leu—Thr—Cha—Ile—Trp—OH |
| 40 | 68 | 20 | Gly—Asn—Trp—His—Gly—Thr—Ala—Pro—Asp—Trp—Val—Tyr—Phe—Ala—His—Leu—Thr—Leu—Ile—Trp—OH |
| 41 | 69 | 20 | Gly—Asn—Trp—His—Gly—Thr—Ala—Pro—Asp—Trp—Val—Tyr—Phe—Ala—His—Leu—Thr—Thi—Ile—Trp—OH |
| 42 | — | 20 | H—Gly—Asn—Trp—His—Gly—Thr—Ala—Pro—Asp—Trp—Val—Tyr—Phe—Ala—His—Leu—Thr—Thi—Ile—D-Trp—OH |
| 43 | 37 | 20 | H—Gly—Asn—Trp—His—Gly—Thr—Ala—Pro—Asp—Trp—Val—Tyr—Phe—Ala—His—Leu—Glu—Ile—Ile—Trp—OH |
| 44 | — | 20 | H—Gly—Asn—Trp—His—Gly—Thr—Ala—Pro—Asp—Trp—Val—Tyr—Phe—Ala—D-Trp—Nva—Glu—Ile—D-Ile—Trp—OH |
| 45 | — | 20 | H—Gly—Asn—Trp—His—Gly—Thr—Ala—Pro—Asp—Trp—Val—Tyr—Phe—Ala—His—Leu—Ser—Met—Ile—Trp—OH |
| 46 | 38 | 20 | H—Gly—Asn—Trp—His—Gly—Thr—Ala—Ala—Asp—Trp—Val—Tyr—Phe—Ala—His—Leu—Ser—Met—Ile—Trp—OH |
| 47 | 39 | 20 | H—Gly—Asn—Trp—His—Gly—Thr—Ala—Pro—Asp—Trp—Val—Tyr—Pro—Tyr—Phe—Ala—His—Leu—Asp—Ile—Trp—OH |
| 48 | 40 | 20 | H—Gly—Asn—Trp—His—Gly—Thr—Ala—Pro—Asp—Trp—Pro—Tyr—Phe—Ala—His—Leu—Thr—Thi—Ile—Trp—OH |
| 49 | 41 | 19 | CH$_3$CONHCH$_2$SCH$_2$CH$_2$CO—Asn—Trp—His—Gly—Thr—Ala—Pro—Cys—Trp—Val—Tyr—Phe—Ala—His—Leu—Ser—Met—Ile—Trp—OH |
| 50 | 70 | 19 | SCH$_2$CH$_2$CO—Asn—Trp—His—Gly—Thr—Ala—Pro—Cys—Trp—Val—Tyr—Phe—Ala—His—Leu—Ser—Met—Ile—Trp—OH |
| 51 | 71 | 19 | Gly—Phe—Ile—Gly—Trp—Gly—Asn—Asp—Trp—Val—Tyr—Phe—Ala—His—Leu—Asp—Ile—Ile—Trp—OH |
| 52 | 72 | 20 | Gly—Tyr—Pro—Trp—Trp—Asn—Tyr—Arg—Asp—Trp—Val—Tyr—Phe—Ala—His—Leu—Asp—Ile—Ile—Trp—OH |
| 53 | 73 | 19 | Gly—Ser—Ala—Ala—Val—Tyr—Phe—Asp—Trp—Val—Tyr—Phe—Ala—His—Leu—Asp—Ile—Ile—Trp—OH |
| 54 | 59 | 19 | H—Gly—Phe—Ile—Gly—Trp—Gly—Asn—Asp—Trp—Val—Tyr—Phe—Ala—His—Leu—Asp—Ile—Ile—Trp—OH |
| 55 | 60 | 19 | H—Gly—Ser—Ala—Ala—Val—Tyr—Phe—Asp—Trp—Val—Tyr—Phe—Ala—His—Leu—Asp—Ile—Ile—Trp—OH |

The endothelin receptor-antagonizing activity and the inhibitory effect on ET-1 contraction of Compound (I) are described below by test examples.

Test Example 1: Endothelin Receptor-Antagonizing Activity

Bovine cerebellum tissue was homogenized at 4° C. by using POLYTRON (type PT10/35, manufactured by Kinematic Gmbh Co.) in a buffer solution A (1 mM $NaHCO_3$, 5 mM ethylenediaminetetraacetic acid, 5 µg/ml leupeptin, 5 µg/ml pepstatin A, 40 µM phenylmethylsulfonyl fluoride, pH 8.3).

The obtained suspension was centrifuged for 10 minutes at 8,000 G and 4° C., and the resulting supernatant was centrifuged for 60 minutes at 40,000 G and 4° C. to obtain pellets. The obtained pellets were suspended in a buffer solution A and again centrifuged for 60 minutes at 40,000 G and 4° C. The resulting solid substance was prepared as a suspension containing 2 mg/ml of protein, and the suspension was used as a membrane fraction liquid. A membrane fraction solution was prepared by adding 7 µl of the membrane fraction liquid per 1 ml of a buffer solution B (50 mM Tris-HCl, 1 mM ethylenediaminetetraacetic acid, 0.2% bovine serum albumin, pH 7.6). $^{125}$I-Endothelin-1 (approx. 30,000 cpm) was added to the membrane fraction solutions containing unlabelled ET-1 (final concentration 100 nM) or any one of the compounds shown in Table 2, or containing neither of them. These mixtures were incubated at 25° C. for 2 hours, and then filtered with a GF/B glass filter (produced by Whatman Co.). After washing the filter with a buffer solution C (50 mM tris-HCl, 1 mM ethylenediamine-tetraacetic acid, pH 7.6), the radioactivity on the glass filter was measured to determine the amount of the receptor and the non-specific bound $^{125}$I-endothelin. The inhibition ratio against endothelin receptor binding activity was calculated according to the following equation:

Inhibition ratio (%)=(C−A/C−B)×100

A: Radioactivity in the presence of one of the compounds shown in Table 2

B: Radioactivity in the presence of unlabelled endothelin-1

C: Radioactivity in the absence of both of the compound shown in Table 2 and unlabelled endothelin-1

The results are shown in Table 2.

TABLE 2

| Compound No. | $IC_{50}$ (nM) |
|---|---|
| 1 | 0.14 |
| 2 | 0.061 |
| 3 | 0.064 |
| 4 | 0.22 |
| 5 | 11 |
| 6 | 0.11 |
| 7 | 0.10 |
| 8 | 0.076 |
| 9 | 0.088 |
| 10 | 0.57 |
| 11 | 6.1 |
| 13 | 2.9 |
| 14 | 12 |
| 15 | 0.11 |
| 16 | 5.4 |
| 17 | 0.12 |
| 18 | 1.7 |
| 19 | 1.2 |

TABLE 2-continued

| Compound No. | $IC_{50}$ (nM) |
|---|---|
| 20 | 12 |
| 21 | 0.96 |
| 22 | 0.12 |
| 23 | 54 |
| 24 | 50 |
| 25 | 0.58 |
| 26 | 0.63 |
| 27 | 4.9 |
| 28 | 89 |
| 29 | 0.37 |
| 30 | 170 |
| 31 | 210 |
| 33 | 0.16 |
| 35 | 1.6 |
| 37 | 8.7 |
| 39 | 280 |
| 40 | 34 |
| 41 | 2.5 |
| 42 | 210 |
| 43 | 17 |
| 44 | 290 |
| 45 | 3.3 |
| 46 | 0.8 |
| 47 | 4.2 |
| 48 | 5.0 |
| 51 | 3.3 |
| 52 | 19 |
| 53 | 2.4 |
| w | >1000 |

$IC_{50}$: Concentration causing 50% inhibition of endothelin-1 binding

Test Example 2: Inhibitory Effect On ET-1 Contraction (ring specimen of extracted rat thoracic aorta)

Male Sprague-Dawley rats (Slc. 450–550 g) were anesthetized by intravenous injection of 50 mg/kg of sodium pentobarbital (Nembutal™, Dynabot), and the heads thereof were then incised to die by bleeding. The breasts of the rats were then incised to extract the thoracic aortas therefrom. After the connective tissue which adhered to the blood vessels were removed in a nutrient solution, the blood vessels were cut into rings (3–4 mm), and two metallic holders (one of which was fixed to a support rod) were passed through the blood vessel to prepare a specimen. One end of the holder was mounted on a tension transducer (TB-611T, produced by Nihon Koden) through silk yarn, and the specimen was suspended in a Magnus' tube containing a nutrient solution. Resting tension (1.5 g) was applied to the specimen, and the nutrient solution was replaced several times until the tension was stabilized. Norepinephrine [(±) hydrochloride, Sigma] (10–20 µM) was then added, and the tension generated by contraction of the specimen was measured to determine the maximum value of the tension. The tension generated was detected by the tension transducer, amplified by a pressure strain amplifier (AP-621G, produced by Nihon Koden) and then recorded by a pen recorder (TYPE3066, YOKOGAWA). After the specimen was washed several times to remove Norepinephrine, each of the compounds shown in Table 3 which was dissolved in distilled water was added to the nutrient solution so that the concentration thereof was $10^{-7}$M, or only distilled water was added thereto in the same volume. Krebs-Henseleit solution [composition (mM): NaCl 119; KCl 4.7; $MgSO_4 \cdot 7H_2O$ 1.2; $CaCl_2 \cdot 2H_2O$ 1.8; $KH_2PO_4$ 1.2; $NaHCO_3$ 24.9; Glucose 11.1] through which 95% $O_2$+5% $CO_2$ had been passed for 30 minutes or more was used as the nutrient solution (37° C.). After the specimens were allowed to stand for 10 minutes, ET-1 was successively added to the nutrient solutions so that the concentration thereof was $3\times10^{-9}$M, and the tension of each of the specimens was measured. The relative value to the maximum tension previously determined was calculated, and the inhibitory effect (% inhibition) on contraction due to ET-1 was determined according to the following equation. The results are shown in Table 3.

% inhibition=(A−B/A)×100

A: Relative value of tension when only distilled water was added

B: Relative value of tension when a compound shown in Table 3 was added

TABLE 3

| Compound No. | % inhibition |
| --- | --- |
| 14 | 47.0 |
| 17 | 61.3 |
| 21 | 40.4 |

Examples and Reference Examples of the present invention are described below.

BEST MODE FOR CARRYING OUT THE INVENTION

In Examples 1 to 50 and Reference Examples 1, 3, 4 and 5 below, peptides were synthesized by operating a peptide synthesizer PSSM-8 manufactured by Shimazu Seisakusho in accordance with the synthetic program of the same company. The condensation reaction of amino acids was performed under the standard conditions according to the Fmoc method (Fundamentals and Experiments in Peptide Synthesis, Nobuo Izumiya et al., Maruzen).

In Reference Examples 2 and 6, peptides were synthesized by operating a peptide synthesizer 430A manufactured by Applied Biosystems, Inc., U.S.A. (ABI Co.) in accordance with the synthetic program of the same company. The condensation reaction of amino acids was performed under the standard conditions using symmetrical acid anhydride.

Example 1: Synthesis of Compound 1

Compound a (200 μg) obtained in Reference Example 1 was dissolved in 100 μl of DMF, and then 120 μg of succinic anhydride was added thereto under ice cooling, followed by stirring under ice cooling for 1 hour and at room temperature for 21 hours. The obtained solution containing intended substance was purified by reverse phase HPLC to give 40 μg of Compound 1.

MS analysis [FABMS]: 2497 (M+H)

Example 2: Synthesis of Compound 2

Synthesis was effected according to the same method as in Reference Example 1 except for using 20 mg of a carrier resin to which 10.4 μmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Thr(t-Bu)-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 39.4 mg of the crude peptide. This crude peptide was purified by reverse phase HPLC, and then freeze-dried to give 17.9 mg of the purified product.

MS analysis [FABMS]: 2441 (M+H)

Amino acid analysis: Found (Theoretical) Gly 1.2 (1), Ala 2.0 (2), Asx 2.0 (3), His 2.0 (2), Ile 1.0 (2), Leu 1.0 (1), Pro 1.3 (1), Thr 2.0 (2), Tyr 0.9 (1), Val 0.8 (1), Phe 1.0 (1), Trp not analyzed Example 3: Synthesis of Compound 3

Synthesis was effected according to the same method as in Reference Example 1 except for using 20 mg of a carrier resin to which 10.4 μmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Gly-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 41.5 mg of the crude peptide. This crude peptide was purified by reverse phase HPLC, and then freeze-dried to give 21.3 mg of the purified product.

MS analysis [FABMS]: 2353 (M+H)

Amino acid analysis: Found (Theoretical) Gly 3.8 (3), Ala 2.0 (2), Asx 2.3 (3), His 2.1 (2), Ile 0.8 (2), Leu 0.8 (1), Pro 1.4 (1), Tyr 0.7 (1), Val 0.6 (1), Phe 0.8 (1), Trp not analyzed Example 4: Synthesis of Compound 4

Synthesis was effected according to the same method as in Reference Example 1 except for using 20 mg of a carrier resin to which 10.4 μmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Ala-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 42.0 mg of the crude peptide. This crude peptide was purified by reverse phase HPLC, and then freeze-dried to give 16.6 mg of the purified product.

MS analysis [FABMS]: 2282 (M+H)

Amino acid analysis: Found (Theoretical) Gly 2.4 (2), Ala 3.0 (3), Asx 2.5 (3), His 2.2 (2), Ile 1.0 (2), Leu 0.9 (1), Pro 1.3 (1), Thr 1.2 (1), Tyr 0.8 (1), Val 0.8 (1), Phe 0.9 (1), Trp not analyzed Example 5: Synthesis of Compound 5

Synthesis was effected according to the same method as in Reference Example 1 except for using 20 mg of a carrier resin to which 10.2 μmol of Fmoc-Phe was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 41.6 mg of the crude peptide. This crude peptide was purified by reverse phase HPLC, and then freeze-dried to give 16.6 mg of the purified product.

MS analysis [FABMS]: 2358 (M+H)

Amino acid analysis: Found (Theoretical) Gly 2.8 (2), Ala 2.0 (2), Asx 2.5 (3), His 2.1 (2), Ile 0.7 (2), Leu 0.7 (1), Pro 1.5 (1), Thr 1.4 (1), Tyr 0.6 (1), Val 0.5 (1), Phe 1.3 (2), Trp not analyzed Example 6: Synthesis of Compound 6

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ser(t-Bu)-OH, Fmoc-Thr(t-Bu)-OH, Fmoc-Gly-OH, Fmoc-Lys(Boc)-OH, Fmoc-Trp-OH, Fmoc-Asp(Ot-Bu)-OH, and Fmoc-Gly-OH. The peptide produced was separated from the resin by the same method as in Reference Example 1 to give 26.8 mg of the crude peptide. This crude peptide was purified by reverse phase HPLC, and then freeze-dried to give 6.3 mg of the purified product.

MS analysis [FABMS]: 2405 (M+H)

Amino acid analysis: Found (Theoretical) Gly 2.2 (2), Ala 1.0 (1), Asx 2.3 (3), His 1.0 (1), Ile 0.9 (2), Leu 1.0 (1), Pro 1.5 (1), Thr 1.0 (1), Tyr 0.8 (1), Val 0.8 (1), Phe 0.9 (1), Ser 1.2 (1), Lys 1.3 (1), Trp not analyzed Example 7: Synthesis of Compound 7

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, and Fmoc-Asn(Trt)-OH. The peptide produced was separated from the resin by the same method as in Reference Example 1 to give 29.3 mg of the crude peptide. This crude peptide was purified by reverse phase HPLC, and then freeze-dried to give 4.6 mg of the purified product.

MS analysis [FABMS]: 2340 (M+H)

Amino acid analysis: Found (Theoretical) Gly 1.1 (1), Ala 2.0 (2), Asx 2.4 (3), His 2.0 (2), Ile 0.8 (2), Leu 0.8 (1), Pro 1.3 (1), Thr 1.2 (1), Tyr 0.7 (1), Val 0.7 (1), Phe 0.8 (1), Trp not analyzed Example 8: Synthesis of Compound 8

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, and Fmoc-Trp-OH. The peptide produced was separated from the resin by the same method as in Reference Example 1 to give 24.9 mg of the crude peptide. This crude peptide was purified by reverse phase HPLC, and then freeze-dried to give 8.7 mg of the purified product.

MS analysis [FABMS]: 2226 (M+H)

Amino acid analysis: Found (Theoretical) Gly 1.0 (1), Ala 2.0 (2), Asx 1.2 (2), His 2.1 (2), Ile 0.8 (2), Leu 0.8 (1), Pro 1.1 (1), Thr 1.1 (1), Tyr 0.8 (1), Val 0.7 (1), Phe 0.8 (1), Trp not analyzed Example 9: Synthesis of Compound 9

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, and Fmoc-His(Trt)-OH. The peptide produced was separated from the resin by the same method as in Reference Example 1 to give 24.7 mg of the crude peptide. This crude peptide was purified by reverse phase HPLC, and then freeze-dried to give 11.5 mg of the purified product.

MS analysis [FABMS]: 2040 (M+H)

Amino acid analysis: Found (Theoretical) Gly 1.1 (1), Ala 2.0 (2), Asx 1.2 (2), His 2.0 (2), Ile 0.7 (2), Leu 0.8 (1), Pro 1.2 (1), Thr 1.2 (1), Tyr 0.7 (1), Val 0.6 (1), Phe 0.8 (1), Trp not analyzed Example 10: Synthesis of Compound 10

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 43.4 mg of the crude peptide. This crude peptide was purified by reverse phase HPLC, and then freeze-dried to give 5.8 mg of the purified product.

MS analysis [FABMS]: 2298 (M+H)

Amino acid analysis: Found (Theoretical) Gly 2.1 (2), Ala 2.0 (2), Asx 1.6 (3), His 2.1 (2), Ile 1.0 (2), Leu 0.9 (1), Pro 1.1 (1), Thr 1.1 (1), Tyr 0.9 (1), Phe 0.9 (1), Trp not analyzed Example 11: Synthesis of Compound 11

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 42.7 mg of the crude peptide. This crude peptide was purified by reverse phase HPLC, and then freeze-dried to give 10.3 mg of the purified product.

MS analysis [FABMS]: 2135 (M+H)

Amino acid analysis: Found (Theoretical) Gly 2.1 (2), Ala 2.0 (2), Asx 2.0 (3), His 2.1 (2), Ile 0.9 (2), Leu 0.9 (1), Pro 1.2 (1), Thr 1.0 (1), Phe 0.9 (1), Trp not analyzed

Example 12: Synthesis of Compound 12

Synthesis was effected according to the same method as in Reference Example 1 except for using 30 mg of a carrier resin to which 15.6 μmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, and Fmoc-Trp-OH. The peptide produced was separated from the resin by the same method as in Reference Example 1 to give 40.5 mg of the crude peptide. This crude peptide was purified by reverse phase HPLC, and then freeze-dried to give 10.9 mg of the purified product.

MS analysis [FABMS]: 1462 (M+H)

Amino acid analysis: Found (Theoretical) Ala 1.0 (1), Asx 0.9 (1), His 1.0 (1), Ile 0.8 (2), Leu 0.9 (1), Tyr 0.8 (1), Val 0.7 (1), Phe 0.9 (1), Trp not analyzed

Example 13: Synthesis of Compound 13

Synthesis was effected according to the same method as in Reference Example 1 except for using 20 mg of a carrier resin to which 10.4 μmol of Fmoc-Trp was bound, and successively using as N-protected amino acids Fmoc-Ile-OH, Fmoc-Leu-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 29.4 mg of the crude peptide. This crude peptide was purified by reverse phase HPLC, and then freeze-dried to give 14.1 mg of the purified product.

MS analysis [FABMS]: 2383 (M+H)

Amino acid analysis: Found (Theoretical) Gly 2.0 (2), Ala 2.0 (2), Asx 1.3 (2), His 2.2 (2), Ile 1.1 (1), Leu 2.3 (2), Pro 1.2 (1), Thr 2.0 (2), Tyr 0.8 (1), Val 0.8 (1), Phe 0.9 (1), Trp not analyzed

Example 14: Synthesis of Compound 14

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Cha-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give the crude peptide. This crude peptide was purified by reverse phase HPLC, and then freeze-dried to give 6.3 mg of the purified product.

MS analysis [FABMS]: 2423 (M+H)

Amino acid analysis: Found (Theoretical) Gly 2.1 (2), Ala 2.0 (2), Asx 1.2 (2), His 2.1 (2), Ile 1.1 (1), Leu 1.1 (1), Pro 1.2 (1), Thr 2.0 (2), Tyr 0.9 (1), Val 0.8 (1), Phe 1.0 (1), Trp and Cha not analyzed

Example 15: Synthesis of Compound 15

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Abu-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give the crude peptide. This crude peptide was purified by reverse phase HPLC, and then freeze-dried to give 5.2 mg of the purified product.

MS analysis [FABMS]: 2355 (M+H)

Amino acid analysis: Found (Theoretical) Gly 2.1 (2), Ala 2.0 (2), Asx 1.3 (2), His 2.2 (2), Ile 1.1 (1), Leu 1.2 (1), Pro 1.2 (1), Thr 2.2 (2), Tyr 1.0 (1), Val 1.0 (1), Phe 1.1 (1), Trp and Abu not analyzed

Example 16: Synthesis of Compound 16

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Leu-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give the crude peptide. This crude peptide was purified by reverse phase HPLC, and then freeze-dried to give 8.2 mg of the purified product.

MS analysis [FABMS]: 2397 (M+H)

Amino acid analysis: Found (Theoretical) Gly 2.1 (2), Ala 2.0 (2), Asx 2.2 (3), His 2.1 (2), Ile 0.9 (1), Leu 1.9 (2), Pro 1.3 (1), Thr 1.2 (1), Tyr 0.8 (1), Val 0.8 (1), Phe 1.0 (1), Trp not analyzed

Example 17: Synthesis of Compound 17

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Thi-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 31.3 mg of the crude peptide. This crude peptide was purified by reverse phase HPLC, and then freeze-dried to give 7.6 mg of the purified product.

MS analysis [FABMS]: 2423 (M+H)

Amino acid analysis: Found (Theoretical) Gly 1.9 (2), Ala 2.0 (2), Asx 1.2 (2), His 2.1 (2), Ile 1.0 (1), Leu 1.0 (1), Pro 1.1 (1), Thr 2.0 (2), Tyr 1.0 (1), Val 0.9 (1), Phe 1.0 (1), Trp and Thi not analyzed

Example 18: Synthesis of Compound 18

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Met-OH, Fmoc-Thr (t-Bu)-OH, Fmoc-Leu-OH, Fmoc-His (Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His (Trt)-OH, Fmoc-Trp-OH, Fmoc-Asn(Trt)-OH, and Fmoc-Gly-OH. The peptide produced was separated from the resin by the same method as in Reference Example 1 to give 29.9 mg of the crude peptide. This crude peptide was purified by reverse phase HPLC, and then freeze-dried to give 7.1 mg of the purified product.

MS analysis [FABMS]: 2401 (M+H)

Amino acid analysis: Found (Theoretical) Gly 2.0 (2), Ala 2.0 (2), Asx 1.3 (2), His 2.2 (2), Ile 1.2 (1), Leu 1.1 (1), Pro 1.2 (1), Thr 2.2 (2), Tyr 1.0 (1), Val 0.9 (1), Phe 1.0 (1), Met 1.0 (1), Trp not analyzed Example 19: Synthesis of Compound 19

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Tyr(t-Bu)-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 23.7 mg of the crude peptide. This crude peptide was purified by reverse phase HPLC, and then freeze-dried to give 7.4 mg of the purified product.

MS analysis [FABMS]: 2433 (M+H)

Amino acid analysis: Found (Theoretical) Gly 1.9 (2), Ala 2.0 (2), Asx 1.1 (2), His 2.0 (2), Ile 0.9 (1), Leu 1.0 (1), Pro 1.0 (1), Thr 1.9 (2), Tyr 1.8 (2), Val 0.8 (1), Phe 0.9 (1), Trp not analyzed Example 20: Synthesis of Compound 20

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Tyr(t-Bu)-OH, Fmoc-Asn(Trt)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 28.4 mg of the crude peptide. This crude peptide was purified by reverse phase HPLC, and then freeze-dried to give 13.8 mg of the purified product.

MS analysis [FABMS]: 2446 (M+H)

Amino acid analysis: Found (Theoretical) Gly 1.9 (2), Ala 2.0 (2), Asx 2.2 (3), His 2.0 (2), Ile 0.9 (1), Leu 1.0 (1), Pro 1.2 (1), Thr 1.0 (1), Tyr 1.7 (2), Val 0.9 (1), Phe 0.9 (1), Trp not analyzed Example 21: Synthesis of Compound 21

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Met-OH, Fmoc-Ser(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 22.9 mg of the crude peptide. This crude peptide was purified by reverse phase HPLC, and then freeze-dried to give 6.5 mg of the purified product.

MS analysis [FABMS]: 2387 (M+H)

Amino acid analysis: Found (Theoretical) Gly 2.0 (2), Ala 2.0 (2), Asx 1.2 (2), His 2.1 (2), Ile 1.0 (1), Leu 1.0 (1), Pro 1.1 (1), Thr 1.0 (1), Tyr 0.9 (1), Val 0.9 (1), Phe 1.0 (1), Ser 1.0 (1), Met 1.0 (1), Trp not analyzed Example 22: Synthesis of Compound 22

Synthesis was effected according to the same method as in Reference Example 1 except for using 40 mg of a carrier resin to which 25.2 μmol of Fmoc-Trp was bound, and successively using as N-protected amino acids Fmoc-Ile-OH, Fmoc-Thi-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ser(t-Bu)-OH, Fmoc-Thr(t-Bu)-OH, Fmoc-Gly-OH, Fmoc-Lys(Boc)-OH, Fmoc-Trp-OH, Fmoc-Asp(Ot-Bu)-OH, and Fmoc-Gly-OH. The peptide produced was separated from the resin by the same method as in Reference Example 1 to give 46.5 mg of the crude peptide. This crude peptide was purified by reverse phase HPLC, and then freeze-dried to give 14.4 mg of the purified product.

MS analysis [FABMS]: 2431 (M+H)

Amino acid analysis: Found (Theoretical) Gly 2.1 (2), Ala 1.0 (1), Asx 1.2 (2), His 1.0 (1), Ile 0.8 (1), Leu 1.1 (1), Pro 1.3 (1), Thr 2.0 (2), Tyr 0.8 (1), Val 0.7 (1), Phe 1.0 (1), Ser 1.0 (1), Lys 1.1 (1), Trp and Thi not analyzed Example 23: Synthesis of Compound 23

Synthesis was effected according to the same method as in Reference Example 1 except for using 50 mg of a carrier resin to which 30.0 μmol of Fmoc-Trp was bound, successively using as N-protected amino acids Fmoc-Ile-OH, Fmoc-MeLeu-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH, and extending the time for stirring in step (d) from 30 minutes to 11 hours in condensation of the third protected amino acid Fmoc-Thr(t-Bu)-OH. The peptide produced was separated from the resin by the same method as in Reference Example 1 to give 45.3 mg of the crude peptide. This crude peptide was purified by reverse phase HPLC, and then freeze-dried to give 2.0 mg of the purified product.

MS analysis [FABMS]: 2397 (M+H)

Amino acid analysis: Found (Theoretical) Gly 2.5 (2), Ala 2.0 (2), Asx 1.3 (2), His 2.1 (2), Ile 1.1 (1), Leu 1.1 (1), Pro 1.0 (1), Thr 2.2 (2), Tyr 1.1 (1), Val 0.9 (1), Phe 1.1 (1), Trp and MeLeu not analyzed

Example 24: Synthesis of Compound 24

Synthesis was effected according to the same method as in Reference Example 1 except for using 50 mg of a carrier resin to which 30.0 μmol of Fmoc-Trp was bound, successively using as N-protected amino acids Fmoc-Ile-OH, Fmoc-MeIle-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH, and condensing the third protected amino acid Fmoc-Thr(t-Bu)-OH according to the same method as in Example 23. The peptide produced was separated from the resin by the same method as in Reference Example 1 to give 28.6 mg of the crude peptide. This crude peptide was purified by reverse phase HPLC, and then freeze-dried to give 0.6 mg of the purified product.

MS analysis [FABMS]: 2397 (M+H)

Amino acid analysis: Found (Theoretical) Gly 1.5 (2), Ala 2.0 (2), Asx 1.5 (2), His 2.3 (2), Ile 1.2 (1), Leu 1.1 (1), Pro 1.1 (1), Thr 2.1 (2), Tyr 1.2 (1), Val 1.0 (1), Phe 1.2 (1), Trp and MeIle not analyzed

Example 25: Synthesis of Compound 25

Synthesis was effected according to the same method as in Reference Example 1 except for using 30 mg of a carrier resin to which 18.9 μmol of Fmoc-Trp was bound, and successively using as N-protected amino acids Fmoc-Ile-OH, Fmoc-Phg-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 37.0 mg of the crude peptide. This crude peptide was purified by reverse phase HPLC, and then freeze-dried to give 2.2 mg of the purified product.

MS analysis [FABMS]: 2403 (M+H)

Amino acid analysis: Found (Theoretical) Gly 2.1 (2), Ala 2.0 (2), Asx 1.0 (2), His 2.1 (2), Ile 1.7 (1), Leu 0.9 (1), Pro 1.0 (1), Thr 2.0 (2), Tyr 0.9 (1), Val 0.8 (1), Phe 0.9 (1), Trp and Phg not analyzed

Example 26: Synthesis of Compound 26

Synthesis was effected according to the same method as in Reference Example 1 except for using 30 mg of a carrier resin to which 18.9 μmol of Fmoc-Trp was bound, and successively using as N-protected amino acids Fmoc-Ile-OH, Fmoc-Nle-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 30.3 mg of the crude peptide. This crude peptide was purified by reverse phase HPLC, and then freeze-dried to give 5.5 mg of the purified product.

MS analysis [FABMS]: 2383 (M+H)

Amino acid analysis: Found (Theoretical) Gly 2.3 (2), Ala 2.0 (2), Asx 1.3 (2), His 2.2 (2), Ile 1.0 (1), Leu 1.0 (1), Pro 1.2 (1), Thr 2.2 (2), Tyr 0.8 (1), Val 0.8 (1), Phe 0.9 (1), Trp and Nle not analyzed

Example 27: Synthesis of Compound 27

Synthesis was effected according to the same method as in Reference Example 1 except for using 30 mg of a carrier resin to which 18.9 μmol of Fmoc-Trp was bound, and successively using as N-protected amino acids Fmoc-Ile-OH, Fmoc-Thi-OH, Fmoc-Thr(t-Bu)-OH, Fmoc-Leu-OH, Fmoc-His(Trt)-OH, Fmoc-D-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 35.0 mg of the crude peptide. This crude peptide was purified by reverse phase HPLC, and then freeze-dried to give 7.7 mg of the purified product.

MS analysis [FABMS]: 2423 (M+H)

Amino acid analysis: Found (Theoretical) Gly 2.0 (2), Ala 2.0 (2), Asx 1.0 (2), His 2.2 (2), Ile 0.9 (1), Leu 1.0 (1), Pro 1.1 (1), Thr 1.9 (2), Tyr 0.9 (1), Val 0.8 (1), Phe 1.0 (1), Trp and Thi not analyzed

Example 28: Synthesis of Compound 28

Synthesis was effected according to the same method as in Reference Example 1 except for using 30 mg of a carrier resin to which 18.9 μmol of Fmoc-Trp was bound, and successively using as N-protected amino acids Fmoc-Ile-OH, Fmoc-Thi-OH, Fmoc-Thr (t-Bu) -OH, Fmoc-Leu-OH, Fmoc-D-Trp-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 41.0 mg of the crude peptide. This crude peptide was purified by reverse phase HPLC, and then freeze-dried to give 15.7 mg of the purified product.

MS analysis [FABMS]: 2472 (M+H)

Amino acid analysis: Found (Theoretical) Gly 2.2 (2), Ala 2.0 (2), Asx 1.5 (2), His 1.2 (1), Ile 0.8 (1), Leu 0.9 (1), Pro 1.1 (1), Thr 1.9 (2), Tyr 0.8 (1), Val 0.7 (1), Phe 0.9 (1), Trp and Thi not analyzed

Example 29: Synthesis of Compound 29

Synthesis was effected according to the same method as in Reference Example 1 except for using 30 mg of a carrier resin to which 18.9 μmol of Fmoc-Trp was bound, and successively using as N-protected amino acids Fmoc-Ile-OH, Fmoc-Thi-OH, Fmoc-Thr(t-Bu)-OH, Fmoc-Nva-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 49.3 mg of the crude peptide. This crude peptide was purified by reverse phase HPLC, and then freeze-dried to give 12.6 mg of the purified product.

MS analysis [FABMS]: 2409 (M+H)

Amino acid analysis: Found (Theoretical) Gly 2.1 (2), Ala 2.0 (2), Asx 1.2 (2), His 2.1 (2), Ile 0.9 (1), Pro 1.1 (1), Thr 1.9 (2), Tyr 0.9 (1), Val 0.7 (1), Phe 1.0 (1), Trp, Thi, and Nva not analyzed

Example 30: Synthesis of Compound 30

Synthesis was effected according to the same method as in Reference Example 1 except for using 30 mg of a carrier resin to which 18.9 µmol of Fmoc-Trp was bound, and successively using as N-protected amino acids Fmoc-Ile-OH, Fmoc-Thi-OH, Fmoc-Gly-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 57.5 mg of the crude peptide. This crude peptide was purified by reverse phase HPLC, and then freeze-dried to give 15.0 mg of the purified product.

MS analysis [FABMS]: 2379 (M+H)

Amino acid analysis: Found (Theoretical) Gly 3.0 (3), Ala 2.0 (2), Asx 1.5 (2), His 2.1 (2), Ile 0.7 (1), Leu 0.9 (1), Pro 1.0 (1), Thr 0.9 (1), Tyr 0.9 (1), Val 0.8 (1), Phe 1.0 (1), Trp and Thi not analyzed

Example 31: Synthesis of Compound 31

Synthesis was effected according to the same method as in Reference Example 1 except for using 30 mg of a carrier resin to which 18.9 µmol of Fmoc-Trp was bound, and successively using as N-protected amino acids Fmoc-D-Ile-OH, Fmoc-Thi-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 49.5 mg of the crude peptide. This crude peptide was purified by reverse phase HPLC, and then freeze-dried to give 17.9 mg of the purified product.

MS analysis [FABMS]: 2423 (M+H)

Amino acid analysis: Found (Theoretical) Gly 2.1 (2), Ala 2.0 (2), Asx 1.2 (2), His 2.0 (2), Ile 0.8 (1), Leu 1.0 (1), Pro 1.1 (1), Thr 2.1 (2), Tyr 0.9 (1), Val 0.8 (1), Phe 1.0 (1), Trp and Thi not analyzed

Example 32: Synthesis of Compound 33

Step 1: Synthesis of Compound 32

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Cys(Trt)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Cys(Trt)-OH. The peptide produced was separated from the resin by the same method as in Reference Example 1 to give 39.5 mg of the crude product of Compound 32.

MS analysis [FABMS]: 2431 (M+H)

Step 2: Synthesis of Compound 33

The crude product (20 mg) obtained in step 1 was dissolved in 6 ml of 20% DMSO-water, and then 1 ml of aqueous ammonia (pH 10) was added thereto, followed by being allowed to stand at 4° C. for one week to form a S—S bond. After neutralization with 2M acetic acid, the solution was purified by reverse phase HPLC, and then freeze-dried to give 0.9 mg of Compound 33.

MS analysis [FABMS]: 2429 (M+H)

Amino acid analysis: Found (Theoretical) Gly 1.4 (1), Ala 2.0 (2), Asx 1.7 (2), His 2.2 (2), Ile 0.8 (2), Leu 1.2 (1), Pro 1.1 (1), Thr 1.2 (1), Tyr 0.8 (1), Val 0.8 (1), Phe 0.9 (1), Cys 1.8 (2), Trp not analyzed

Example 33: Synthesis of Compound 35

Step 1: Synthesis of Compound 34

Synthesis was effected according to the same method as in Reference Example 1 except for using 30 mg of a carrier resin to which 18.0 µmol of Fmoc-Trp was bound, and successively using as N-protected amino acids Fmoc-Ile-OH, Fmoc-Thi-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Cys(Trt)-OH, Fmoc-Pro-OH, Fmoc-Ser(t-Bu)-OH, Fmoc-Thr(t-Bu)-OH, Fmoc-Gly-OH, Fmoc-Lys(Boc)-OH, Fmoc-Trp-OH, Fmoc-Asp(O-tBu)-OH, and Fmoc-Cys(Trt)-OH. The peptide produced was separated from the resin by the same method as in Reference Example 1 to give 51.5 mg of the crude product of Compound 34.

MS analysis [FABMS]: 2465 (M+H)

Step 2: Synthesis of Compound 35

The crude product (30 mg) obtained in step 1 was dissolved in 14 ml of 30% DMSO-water, and then 2 ml of aqueous ammonia (pH 10) was added thereto, followed by being allowed to stand at 4° C. for 3 days to form a S—S bond. After neutralization with 2M acetic acid, the solution was purified by reverse phase HPLC, and then freeze-dried to give 2.2 mg of Compound 35.

MS analysis [FABMS]: 2463 (M+H)

Amino acid analysis: Found (Theoretical) Gly 1.2 (1), Ala 1.2 (1), Asx 0.7 (1), His 1.2 (1), Ile 1.0 (1), Leu 1.2 (1), Pro 1.0 (1), Thr 1.9 (2), Tyr 1.0 (1), Val 0.9 (1), Phe 1.1 (1), Cys 1.7 (2), Ser 0.7 (1), Lys 1.1 (1), Trp and Thi not analyzed

Example 34: Synthesis of Compound 37

Step 1: Synthesis of Compound 36

Synthesis was effected according to the same method as in Reference Example 1 except for using 20 mg of a carrier resin to which 12.6 µmol of Fmoc-Trp was bound, and successively using as N-protected amino acids Fmoc-Ile-OH, Fmoc-Leu-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Cys(Trt)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Cys(Trt)-OH. The peptide produced was separated from the resin by the same method as in Reference Example 1 to give 35.1 mg of the crude product of Compound 36.

MS analysis [FABMS]: 2417 (M+H)

Step 2: Synthesis of Compound 37

The crude product (15 mg) obtained in step 1 was dissolved in 7 ml of 25% DMSO-water, and then 1 ml of aqueous ammonia (pH 10) was added thereto, followed by being allowed to stand at 4° C. for 6 days to form a S—S bond. After neutralization with 2M acetic acid, the solution was purified by reverse phase HPLC, and then freeze-dried to give 2.8 mg of Compound 37.

MS analysis [FABMS]: 2415 (M+H)

Amino acid analysis: Found (Theoretical) Gly 1.2 (1), Ala 2.0 (2), Asx 0.7 (1), His 2.4 (2), Ile 1.0 (1), Leu 2.3 (2), Pro 1.2 (1), Thr 1.8 (2), Tyr 1.0 (1), Val 0.8 (1), Phe 1.1 (1), Cys 2.0 (2), Trp not analyzed

Example 35: Synthesis of Compound 39

Step 1: Synthesis of Compound 38

Synthesis was effected according to the same method as in Reference Example 1 except for using 20 mg of a carrier resin to which 12.6 μmol of Fmoc-Trp was bound, and successively using as N-protected amino acids Fmoc-Ile-OH, Fmoc-Cha-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Cys (Trt)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Cys (Trt)-OH. The peptide produced was separated from the resin by the same method as in Reference Example 1 to give 34.2 mg of the crude product of Compound 38.

MS analysis [FABMS]: 2457 (M+H)

Step 2: Synthesis of Compound 39

The crude product (15 mg) obtained in step 1 was dissolved in 7 ml of 25% DMSO-water, and then 1 ml of aqueous ammonia (pH 10) was added thereto, followed by being allowed to stand at 4° C. for 3 days to form a S—S bond. After neutralization with 2M acetic acid, the solution was purified by reverse phase HPLC, and then freeze-dried to give 2.3 mg of Compound 39.

MS analysis [FABMS]: 2455 (M+H)

Amino acid analysis: Found (Theoretical) Gly 1.4 (1), Ala 2.0 (2), Asx 1.0 (1), His 2.0 (2), Ile 1.0 (1), Leu 1.4 (1), Pro 1.2 (1), Thr 1.5 (2), Tyr 1.0 (1), Val 0.9 (1), Phe 1.2 (1), Cys 1.8 (2), Trp and Cha not analyzed

Example 36: Synthesis of Compound 40

Step 1: Synthesis of Compound e (H-Val-Tyr-Phe-Ala-His-Leu-Thr-Leu-Ile-Trp-OBzl: Sequence No. 48)

Compound c (10.5 mg) obtained in Reference Example 3 was dissolved in 2 ml of dry DMF, and then 100 μl each of 32.8 mg/ml HOBt, 126.1 mg/ml PyBOP, and 45 μl/m/NMM prepared with dry DMF was successively added thereto under ice cooling, and further 200 μl of 16.1 mg/ml H-Trp-OBzl hydrochloride was added to the solution, followed by being allowed to stand at 4° C. for 3 days. The insoluble matters were filtered off and the filtrate was purified by reverse phase HPLC by the same method as in Reference Example 1. The column used was a Chemco-pack NUCLEOSIL 5C18 (250×20 mm I.D.) manufactured by Chemco K.K., and the obtained fractions of the intended substance were freeze-dried.

A 20% piperidine solution (1 ml) prepared with dry DMF was added to the freeze-dried product, followed by being allowed to stand at room temperature for 5 minutes. The solution was concentrated until 200 μl under reduced pressure, and diethyl ether was added thereto to precipitate crystals. The crystals were washed with ether and dried under reduced pressure to give 3.41 mg of Compound e.

Step 2: Synthesis of Compound 40

Compound b (3.0 mg) obtained in Reference Example 2 was dissolved in 4.07 ml of dry DMF, and then 1 ml each of 1.1 mg/ml HOBt, 4.2 mg/ml PyBOP, 1.5 μl/ml NMM, and 2.27 mg/ml Compound e obtained in step 1 prepared with dry DMF was successively added thereto under ice cooling, and further 0.3 ml of 7.0 mg/ml Compound b was added to the solution, followed by being allowed to stand at 4° C. for one day. The insoluble matters were filtered off and the filtrate was purified by reverse phase HPLC by the same method as in Step 1. The obtained fractions of the intended substance were freeze-dried to give 6.53 mg of the benzyl ester of Compound 40. Dry DMF (1 ml), a methanol solution (1 ml) saturated with ammonium formate, and further 10% Pd/C (about 2 mg) were added to the obtained benzyl ester, followed by a violent stirring at room temperature. Then, the catalyst was filtered off, and the filtrate was purified by reverse phase HPLC by the same method as in step 1. The fractions containing the intended substances were freeze-dried to give 1.85 mg of Compound 40.

MS analysis [FABMS]: 2365 (M+H)

Amino acid analysis: Found (Theoretical) Asx 1.4 (2), Gly 2.1 (2), His 2.0 (2), Thr 1.9 (2), Ala 2.0 (2), Pro 1.1 (1), Val 0.9 (1), Tyr 0.9 (1), Phe 1.0 (1), Leu 1.9 (2), Ile 1.3 (1), Trp not analyzed

Example 37: Synthesis of Compound 41

Step 1: Synthesis of Compound f (H-Val-Tyr-Phe-Ala-His-Leu-Thr-Thi-Ile-Trp-OBzl: Sequence No. 49)

Compound d (36.8 mg) obtained in Reference Example 4 was dissolved in 4 ml of dry DMF, and then 100 μl each of 45.0 mg/ml HOBt, 172.0 mg/ml PyBOP, 60 μl/ml NMM prepared with dry DMF was successively added thereto under ice cooling, and further 200 μl of 22.0 mg/ml H-Trp-OBzl hydrochloride was added to the solution, followed by being allowed to stand at 4° C. for 2 days. The insoluble matters were filtered off and the filtrate was purified by reverse phase HPLC by the same method as in Reference Example 1. The column used was a Chemco-pack NUCLEOSIL 5C18 (250×20 mm I.D.) manufactured by Chemco K.K., and the obtained fractions of the intended substance were freeze-dried.

A 20% piperidine solution (0.5 ml) prepared with dry DMF was added to the freeze-dried product, followed by being allowed to stand at room temperature for 10 minutes. The solution was concentrated until 200 μl under reduced pressure, and diethyl ether was added thereto to precipitate crystals. The crystals were washed with ether and freeze-dried under reduced pressure to give 10.3 mg of Compound f.

Step 2: Synthesis of Compound 41

Compound b (1.5 mg) obtained in Reference Example 2 was dissolved in 1.74 ml of dry DMF, and then 0.5 ml each of 1.1 mg/ml HOBt, 4.2 mg/ml PyBOP, and 1.5 μl/ml NMM prepared with dry DMF was successively added thereto under ice cooling, and further 0.55 ml of 3.40 mg/ml Compound f obtained in step 1 was added to the solution, followed by being allowed to stand at 4° C. for one day. The insoluble matters were filtered off and the filtrate was purified by reverse phase HPLC by the same method as in Step 1. The obtained fractions of the intended substances were freeze-dried to give 0.76 mg of the benzyl ester of Compound 41. Dry DMF (0.15 ml), a methanol solution (0.15 ml) saturated with ammonium formate, and further 10% Pd/C (about 2 mg) were added to the obtained benzyl ester, followed by a violent stirring at room temperature for one hour. Then, the catalyst was filtered off, and the filtrate was purified by reverse phase HPLC by the same method as in step 1. The fractions containing the intended substances were freeze-dried to give 0.28 mg of Compound 41.

MS analysis [FABMS]: 2405 (M+H)

Amino acid analysis: Found (Theoretical) Asx 2.0 (2), Gly 3.3 (2), His 2.2 (2), Thr 2.2 (2), Ala 2.0 (2), Pro 1.2

(1), Val 1.3 (1), Tyr 1.3 (1), Phe 1.2 (1), Leu 1.4 (1), Ile 1.1 (1), Trp and Thi not analyzed

Example 38: Synthesis of Compound 42

Synthesis was effected according to the same method as in Reference Example 1 except for using 20 mg of a carrier resin to which 10.4 µmol of Fmoc-D-Trp was bound, and successively using as N-protected amino acids Fmoc-Ile-OH, Fmoc-Thi-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, FmoC-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 26.5 mg of the crude peptide. This crude peptide was purified by reverse phase HPLC, and then freeze-dried to give 8.8 mg of the purified product.

MS analysis [FABMS]: 2423 (M+H)

Amino acid analysis: Found (Theoretical) Gly 2.3 (2), Ala 2.0 (2), Asx 1.5 (2), His 2.0 (2), Ile 0.9 (1), Leu 1.0 (1), Pro 1.3 (1), Thr 1.9 (2), Tyr 0.9 (1), Val 0.8 (1), Phe 0.9 (1), Trp and Thi not analyzed

Example 39: Synthesis of Compound 43

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Glu(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 25.8 mg of the crude peptide. This crude peptide was purified by reverse phase HPLC, and then freeze-dried to give 8.6 mg of the purified product.

MS analysis [FABMS]: 2411 (M+H)

Amino acid analysis: Found (Theoretical) Gly 2.2 (2), Ala 2.0 (2), Asx 1.6 (2), Glx 0.9 (1), His 2.1 (2), Thr 0.9 (1), Ile 0.8 (2), Leu 0.8 (1), Pro 1.3 (1), Tyr 0.8 (1), Val 0.6 (1), Phe 0.8 (1), Trp not analyzed

Example 40: Synthesis of Compound 44

Synthesis was effected according to the same method as in Reference Example 1 except for using 20 mg of a carrier resin to which 10.4 µmol of Fmoc-Trp was bound, and successively using as N-protected amino acids Fmoc-D-Ile-OH, Fmoc-Ile-OH, Fmoc-Glu(Ot-Bu)-OH, Fmoc-Nva-OH, Fmoc-D-Trp-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 27.3 mg of the crude peptide. This crude peptide was purified by reverse phase HPLC, and then freeze-dried to give 9.1 mg of the purified product.

MS analysis [FABMS]: 2446 (M+H)

Amino acid analysis: Found (Theoretical) Gly 2.4 (2), Ala 2.0 (2), Asx 1.4 (2), Glx 0.8 (1), His 1.1 (1), Ile 1.0 (2), Pro 1.3 (1), Thr 1.2 (1), Tyr 0.9 (1), Val 0.8 (1), Phe 0.9 (1), Trp and Nva not analyzed

Example 41: Synthesis of Compound 45

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Met-OH, Fmoc-Ser(t-Bu)-OH, Fmoc-Leu-OH, Fmoc-His(Trt)-OH, Fmoc-Ala-OH, Fmoc-D-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 29.0 mg of the crude peptide. This crude peptide was purified by reverse phase HPLC, and then freeze-dried to give 9.5 mg of the purified product.

MS analysis [FABMS]: 2387 (M+H)

Amino acid analysis: Found (Theoretical) Gly 2.6 (2), Ala 2.0 (2), Asx 1.5 (2), His 2.1 (2), Ile 0.7 (1), Leu 0.7 (1), Pro 1.4 (1), Thr 1.3 (1), Tyr 0.7 (1), Val 0.7 (1), Phe 0.8 (1), Ser 0.9 (1), Met 1.1 (1), Trp not analyzed

Example 42: Synthesis of Compound 46

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Met-OH, Fmoc-Ser(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Ala-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 25.8 mg of the crude peptide. This crude peptide was purified by reverse phase HPLC, and then freeze-dried to give 7.4 mg of the purified product.

MS analysis [FABMS]: 2361 (M+H)

Amino acid analysis: Found (Theoretical) Gly 2.2 (2), Ala 3.0 (3), Asx 1.6 (2), His 2.1 (2), Ile 0.8 (1), Leu 1.0 (1), Thr 1.0 (1), Tyr 0.8 (1), Val 0.8 (1), Phe 0.9 (1), Ser 1.2 (1), Met 0.9 (1), Trp not analyzed

Example 43: Synthesis of Compound 47

Synthesis was effected according to the same method as in Reference Example 1 except for using 20 mg of a carrier resin to which 10.4 µmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Pro-OH, Fmoc-Trp-OH, Fmoc-Asp(Ot-Bu)-OH, FmoC-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 26.4 mg of the crude peptide. This crude peptide was purified by reverse phase HPLC, and then freeze-dried to give 5.5 mg of the purified product.

MS analysis [FABMS]: 2395 (M+H)

Amino acid analysis: Found (Theoretical) Gly 2.3 (2), Ala 2.0 (2), Asx 2.4 (3), His 2.0 (2), Ile 0.8 (2), Leu 0.9 (1), Pro 2.5 (2), Thr 1.2 (1), Tyr 0.7 (1), Phe 0.8 (1), Trp not analyzed

Example 44: Synthesis of Compound 48

Synthesis was effected according to the same method as in Reference Example 1 except for using 20 mg of a carrier resin to which 10.4 μmol of Fmoc-Trp was bound, and successively using as N-protected amino acids Fmoc-Ile-OH, Fmoc-Thi-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Pro-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The peptide produced was separated from the resin by the same method as in Reference Example 1 to give 24.5 mg of the crude peptide. This crude peptide was purified by reverse phase HPLC, and then freeze-dried to give 5.6 mg of the purified product.

MS analysis [FABMS]: 2421 (M+H)

Amino acid analysis: Found (Theoretical) Gly 2.2 (2), Ala 2.0 (2), Asx 1.3 (2), His 2.1 (2), Ile 0.7 (1), Leu 0.8 (1), Pro 2.2 (2), Thr 2.1 (2), Tyr 0.8 (1), Phe 0.8 (1), Trp and Thi not analyzed

Example 45: Synthesis of Compound 50

Step 1: Synthesis of Compound 49

Synthesis was effected according to the same method as in Reference Example 1 except for using 20 mg of a carrier resin to which 10.4 μmol of Fmoc-Trp was bound, successively using as N-protected amino acids Fmoc-Ile-OH, Fmoc-Met-OH, Fmoc-Ser(t-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Cys(Trt)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Mpa(Acm)-OH, and not effecting treatment with piperidine in step (b) in the final procedure for condensing Mpa(Acm)-OH. The peptide produced was separated from the resin by the same method as in Reference Example 1 to give 23.0 mg of the crude product of Compound 49.

MS analysis [FABMS]: 2477 (M+H)

Step 2: Synthesis of Compound 50

The crude product (20 mg) obtained in step 1 was dissolved in 1 ml of DMF, and then this solution was dropwise added with stirring to 1.5 ml of a DMF solution containing 10 mg of iodine at room temperature in 45 minutes. After stirring at room temperature for 30 minutes, the reaction solution was cooled to 0° C. An aqueous 0.5M sodium thiosulfate solution was dropwise added thereto until the color of the reaction solution became to be light yellow. The reaction solution was purified by reverse phase HPLC, and then freeze-dried to give 1.0 mg of Compound 50.

MS analysis [FABMS]: 2404 (M+H)

Amino acid analysis: Found (Theoretical) Gly 1.4 (1), Ala 2.0 (2), Asx 0.6 (1), His 2.2 (2), Ile 0.7 (1), Leu 1.2 (1), Pro 1.1 (1), Thr 1.2 (1), Tyr 0.8 (1), Val 0.8 (1), Phe 0.9 (1), Ser 0.9 (1), Met 1.0 (1), Cys 0.9 (1), Trp not analyzed

Example 46: Synthesis of Compound 51

Step 1: Synthesis of Compound j (Fmoc-Gly-Phe-Ile-Gly-Trp-Gly-Asn-OH: Sequence No. 50)

Synthesis of the protected peptide was effected according to the same method as in Reference Example 1 except for using as a starting material 120 mg of a carrier resin to which 61.2 μmol of Fmoc-Asn(Trt) was bound, successively using as N-protected amino acids Fmoc-Gly-OH, Fmoc-Trp-OH, Fmoc-Gly-OH, Fmoc-Ile-OH, Fmoc-Phe-OH, and Fmoc-Gly-OH, and not effecting treatment with piperidine in step (b) in the final procedure for condensing Fmoc-Gly-OH. The peptide produced was separated from the resin by the same method as in Reference Example 1. The crude peptide obtained was purified by HPLC by the same method as in Reference Example 1, and then freeze-dried to give 19.9 mg of Compound j.

Step 2: Synthesis of Compound k (H-Gly-Phe-Ile-Gly-Trp-Gly-Asn-Asp-Trp-OBzl: Sequence No. 51)

(a) A DMF solution (1.1 ml) containing the dipeptide (1.4 mg) obtained in step 2 of Reference Example 2 was added to Compound j (2.9 mg) obtained in step 1, and the resultant solution was cooled to 0° C. DEPC (0.9 μl) and triethylamine (1.3 μl) were successively added to the solution, followed by stirring at 4° C. for 5 days. The solvent was removed under reduced pressure, and the residue was redissolved in DMF. The obtained solution was purified by HPLC by the same method as in Reference Example 1 to give 210 μg of Fmoc-Gly-Phe-Ile-Gly-Trp-Gly-Asn-Asp(Ot-Bu)-Trp-OBzl (Sequence No. 52) as a white powder. The reverse phase column used was YMC-Pack ODS-AM 150×6 mm I.D..

MS analysis [FABMS]: 1419 (M+H)

(b) 98% Formic acid (100 μl) was added to the protected peptide (210 μl) obtained in (a) above, followed by stirring at room temperature for 2.5 hours. Ether was added to the solution, and the white precipitates produced were collected by filtration and dried. 20% Piperidine-DMF (50 μl) was added to the precipitates and the resultant solution was allowed to stand at room temperature for 10 minutes. Ether was added thereto again, and the white precipitates produced were collected by filtration and dried to give 150 μg of Compound k.

Step 3: Synthesis of Compound m

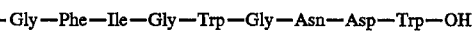

(Compound m)
Gly—Phe—Ile—Gly—Trp—Gly—Asn—Asp—Trp—OH (a) Compound k (150 μg) obtained in step 2 was dissolved in DMF (130 μl), and then a 0.5M DMF solution (1.4 μl) of PyBOP, a 0.5M DMF solution (1.4 μl) of HOBt, and a 0.5M DMF solution (2.4 μl) of NMM were added thereto at room temperature, followed by stirring at room temperature for 7.5 hours. The solvent was removed under reduced pressure, and the residue was purified by HPLC by the same method as in step 2 to give 34 μg of the benzyl ester of Compound m.

(b) The benzyl ester (34 μg) obtained in (a) above was dissolved in DMF (20 μl), and a methanol solution (20 μl) saturated with ammonium formate and 10% Pd/C (about 0.1 mg) were added thereto, followed by stirring at room temperature for 2 hours. Pd/C was filtered off and the obtained solution was purified by HPLC by the same method as in step 2 to give 14 μg of Compound m.

Step 4: Synthesis of Compound 51

(a) Compound m (12 μg) obtained in step 3 was dissolved in DMF (10 μl), and then a 0.1M DMF solution (0.7 μl) of PyBOP, a 0.1M DMF solution (0.7 μl) of HOBt, and a 0.1M DMF solution (1.2 μl) of NMM were added thereto at 0° C. A DMF solution (17 μl) of Compound u (34 μg) obtained in Reference Example 5 was added to the solution, followed by stirring at 4° C. for 18 hours. The solvent was removed under reduced pressure, and the residue was purified by HPLC by the same method as in step 2 to give 18 μg of the benzyl ester of Compound 51.

(b) The benzyl ester (16 µg) obtained in (a) above was dissolved in DMF (10 µl), and then a methanol solution (10 µl) saturated with ammonium formate and 10% Pd/C (about 0.1 mg) were added thereto, followed by stirring at room temperature for 3.5 hours. Pd/C was filtered off and the obtained solution was purified by HPLC by the same method as in step 2 to give 2 µg of Compound 51.

MS analysis [FABMS]: 2290 (M+H)

Amino acid analysis: Found (Theoretical) Asx 1.8 (3), Gly 3.0 (3), His 0.7 (1), Ala 1.0 (1), Tyr 0.7 (1), Val 1.0 (1), Ile 1.6 (3), Leu 1.1 (1), Phe 1.4 (2), Trp not analyzed Example 47: Synthesis of Compound 52

Step 1: Synthesis of Compound n (Fmoc-Gly-Tyr-Pro-Trp-Trp-Asn-Tyr-Arg-OH: Sequence No. 53)

Synthesis of the protected peptide was effected according to the same method as in Reference Example 1 except for using as a starting material 100 mg of a carrier resin to which 57.0 µmol of Fmoc-Arg(Pmc) was bound, successively using as N-protected amino acids Fmoc-Tyr(t-Bu)-OH, Fmoc-Asn(Trt)-OH, Fmoc-Trp-OH, Fmoc-Trp-OH, Fmoc-Pro-OH, Fmoc-Tyr(t-Bu)-OH, and Fmoc-Gly-OH, and not effecting treatment with piperidine in step (b) in the final procedure for condensing Fmoc-Gly. The peptide produced was separated from the resin basically by the same method as in Reference Example 1 except that 400 µl of a mixture of 5 mg/ml 2-methylindole in TFA (82.5%), water (5%), thioanisole (5%), ethylmethylsulfide (3%), 1,2-ethanedithiol (2.5%), and thiophenol (2%) was used and the reaction solution was allowed to stand at room temperature for 6 hours. The crude peptide obtained was purified by HPLC by the same method as in Reference Example 1, and then freeze-dried to give 21.4 mg of Compound n.

Step 2: Synthesis of Compound p (H-Gly-Tyr-Pro-Trp-Trp-Asn-Tyr-Arg-Asp-Trp-OBzl: Sequence No. 54)

(a) Compound n (8.6 mg) obtained in step 1 was dissolved in DMF (3 ml), and then 0.5 ml each of 5.1 mg/ml HOBT, 20.0 mg/ml PyBOP, and 7.0 µl/ml NMM prepared with DMF was successively added thereto at 0° C., and further a DMF solution (0.5 ml) of the dipeptide (7.0 mg/ml) obtained in step 2 of Reference Example 2 was added to the solution, followed by being allowed to stand for 2 hours under ice cooling. After the solvent was removed under reduced pressure, the residue was redissolved in DMF, and the resultant solution was purified by reverse phase HPLC using a reverse phase column (Chemco-pack NUCLEOSIL 5C18, 250×20 mm I.D., manufactured by Chemco K.K.) to give 11.3 mg of Fmoc-Gly-Tyr-Pro-Trp-Trp-Asn-Tyr-Arg-Asp (Ot-Bu)-Trp-OBzl (Sequence No. 55).

(b) To 4.73 mg of the protected peptide obtained in (a) above was added 500 µl of a solution from a mixture of 900 µl of TFA, 50 µl of 1,2-ethanedithiol, 50 µl of anisole, and 5 mg of 2-methylindole, followed by being allowed to stand at room temperature for one hour. Ether was added thereto, and the white precipitates produced were collected by filtration and dried. 20% Piperidine-dry DMF (500 µl) was added to the precipitates, followed by being allowed to stand at room temperature for 5 minutes. Ether was added thereto again, and the white precipitates produced were collectd by filtration and dried to give 3.12 mg of Compound p.

Step 3: Synthesis of Compound q (Compound q, SEQ ID NO.: 74)

Gly—Tyr—Pro—Trp—Trp—Asn—Tyr—Arg—Asp—Trp—OH (a) Compound p (2.17 mg) obtained in step 2 was dissolved in DMF (1.9 ml), and then 100 µl each of 5.8 mg/ml HOBt, 22.2 mg/ml PyBOP, and 7.8 µl ml NMM prepared with DMF was successively added thereto at 0° C., followed by being allowed to stand for 3 hours under ice cooling. The solvent was removed under reduced pressure, and the product obtained was purified by HPLC by the same method as in step 2 to give 806 µg of the benzyl ester of Compound q.

(b) The benzyl ester (800 µg) obtained in (a) above was dissolved in DMF (200 µl), and then a methanol solution (200 µl) saturated with ammonium formate was added thereto, and further a small amount of 10% Pd/C was added to the solution, followed by violent stirring at room temperature for 2 hours. Then, Pd/C was filtered off and the filtrate was purified by HPLC by the same method as in step 2 to give 214 µg of Compound q.

Step 4: Synthesis of Compound 52

(a) Compound q (107 µg) obtained in step 3 was dissolved in DMF (31 µl), and then 50 µl each of 0.61 mg/ml HOBt, 2.3 mg/ml PyBOP, and 0.8 µl/ml NMM prepared with DMF was successively added thereto at 0° C., and further a DMF solution (19 µl) containing 5.8 mg/ml Compound u obtained in Reference Example 5 was added to the solution, followed by being allowed to stand for 3 hours under ice cooling. The solution was purified by HPLC by the same method as in step 2 to give 122 µg of the benzyl ester of Compound 52.

(b) The benzyl ester (122 µg) obtained in (a) above was dissolved in DMF (50 µl), and then a methanol solution (50 µl) saturated with ammonium formate was added thereto, and further a small amount of 10% Pd/C was added to the solution, followed by violent stirring at room temperature for 2 hours. Then, Pd/C was filtered off and the filtrate was purified by HPLC by the same method as in step 2 to give 6.7 µg of Compound 52.

MS analysis [FABMS]: 2681 (M+H)

Amino acid analysis: Found (Theoretical) Asx 2.3 (3), Gly 2.5 (1), His 1.0 (1), Arg 1.0 (1), Ala 1.0 (1), Pro 1.1 (1), Tyr 2.9 (3), Val 0.9 (1), Ile 1.0 (2), Leu 1.0 (1), Phe 1.0 (1), Trp not analyzed Example 48: Synthesis of Compound 53

Step 1: Synthesis of Compound r (Fmoc-Gly-Ser-Ala-Ala-Val-Tyr-Phe-OH: Sequence No. 56)

Synthesis of the protected peptide was effected according to the same method as in Reference Example 1 except for using as a starting material 120 mg of a carrier resin to which 61.2 µmol of Fmoc-Phe was bound, successively using as N-protected amino acids Fmoc-Tyr(t-Bu)-OH, Fmoc-Val-OH, Fmoc-Ala-OH, Fmoc-Ala-OH, Fmoc-Ser(t-Bu)-OH, and Fmoc-Gly-OH, and not effecting treatment with piperidine in step (b) in the final procedure for condensing Fmoc-Gly. The peptide produced was separated from the resin basically by the same method as in Reference Example 1 except that 300 µl of a mixture of TFA (90%), thioanisole (5%), and 1,2-ethanedithiol (5%) was used and the reaction solution was allowed to stand at room temperature for 2 hours. The crude peptide obtained was purified by HPLC by the same method as in Reference Example 1, and then freeze-dried to give 34.0 mg of Compound r.

Step 2: Synthesis of Compound s (H-Gly-Ser-Ala-Ala-Val-Tyr-Phe-Asp-Trp-OBzl: Sequence No. 57)

(a) Compound r (7.81 mg) obtained in step 1 was dissolved in DMF (2 ml), and then 0.5 ml each of 6.8 mg/ml HOBT, 26.0 mg/ml PyBOP, and 9.2 μl/ml NMM prepared with DMF was successively added thereto at 0° C., and further a DMF solution (0.5 ml) of the dipeptide (9.4 mg/ml) obtained in step 2 of Reference Example 2 was added thereto, followed by being allowed to stand for 2 hours under ice cooling. After the solvent was removed under reduced pressure, the residue was redissolved in DMF, and the resultant solution was purified by HPLC to give 11.3 mg of Fmoc-Gly-Ser-Ala-Ala-Val-Tyr-Phe-Asp(Ot-Bu)-Trp-OBzl (Sequence No. 58).

(b) To 350 μg of the protected peptide obtained in (a) above was added 50 μl of a solution from a mixture of 900 μl of TFA, 50 μl of 1,2-ethanedithiol, 50 μl of anisole, and 5 mg of 2-methylindole, followed by being allowed to stand at room temperature for 1 hour. Ether was added thereto, and the white precipitates produced were collected by filtration and dried. 20% Piperidine-dry DMF (50 μl) was added to the precipitates, followed by being allowed to stand at room temperature for 5 minutes. Ether was added thereto again, and the white precipitates produced were collectd by filtration and dried to give 240 μg of Compound s.

Step 3: Synthesis of Compound t (Compound t, SEQ ID NO.: 75)

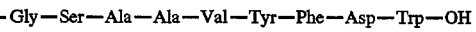
Gly—Ser—Ala—Ala—Val—Tyr—Phe—Asp—Trp—OH (a) Compound s (240 μg) obtained in step 2 was dissolved in DMF (100 μl), and then 50 μl each of 1.8 mg/ml HOBt, 6.8 mg/ml PyBOP, and 2.4 μl/ml NMM prepared with DMF was successively added thereto at 0° C., followed by being allowed to stand for 2 hours under ice cooling. The solvent was removed under reduced pressure, and the product obtained was purified by HPLC by the same method as in step 2 to give 105 μg of the benzyl ester of Compound t.

(b) The benzyl ester (105 μg) obtained in (a) above was dissolved in DMF (50 μl), and then a methanol solution (50 μl) saturated with ammonium formate was added thereto, and further a small amount of 10% Pd/C was added to the solution, followed by violent stirring at room temperature for 2 hours. Then, Pd/C was filtered off and the filtrate was purified by HPLC by the same method as in step 2 to give 111.6 μg of Compound t.

Step 4: Synthesis of Compound 53

(a) To 111.6 μg of Compound t obtained in step 3 was successively added at 0° C. 50 μl each of 0.91 mg/ml HOBt, 3.5 mg/ml PyBOP, and 1.2 μl/ml NMM prepared with DMF, and further 74 μl of a DMF solution of 2.4 mg/ml Compound u obtained in Reference Example 5 was added to the solution, followed by being allowed to stand for 3 hours under ice cooling. The solution was purified by HPLC by the same method as in step 2 to give 128 μg of the benzyl ester of Compound 53.

(b) The benzyl ester (128 μg) obtained in (a) above was dissolved in DMF (50 μl), and then a methanol solution (50 μl) saturated with ammonium formate was added thereto, and further a small amount of 10% Pd/C was added to the solution, followed by violent stirring at room temperature for 2 hours. Then, Pd/C was filtered off and the filtrate was purified by HPLC by the same method as in step 2 to give 11 μg of Compound 53.

MS analysis [FABMS]: 2254 (M+H)

Amino acid analysis: Found (Theoretical) Asx 1.5 (2), Ser 1.4 (1), Gly 1.6 (1), His 1.0 (1), Ala 3.0 (3), Tyr 1.6 (2), Val 1.5 (2), Ile 1.2 (2), Leu 1.0 (1), Phe 1.8 (2), Trp not analyzed Example 49: Synthesis of Compound 54

Synthesis of the protected peptide was effected according to the same method as in Reference Example 1 except for using as a starting material 20 mg of a carrier resin to which 10.4 μmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Asn(Trt)-OH, Fmoc-Gly-OH, Fmoc-Trp-OH, Fmoc-Gly-OH, Fmoc-Ile-OH, Fmoc-Phe-OH, and Fmoc-Gly-OH. The peptide produced was separated from the resin by the same method as in Reference Example 1 to give 45.0 mg of the crude product. This crude product was purified by HPLC by the same method as in Reference Example 1 to give 3.9 mg of Compound 54.

MS analysis [FABMS]: 2308 (M+H)

Amino acid analysis: Found (Theoretical) Asx 2.3 (3), Gly 2.6 (3), His 1.0 (1), Ala 1.0 (1), Tyr 0.9 (1), Val 1.0 (1), Ile 1.8 (3), Leu 1.0 (1), Phe 1.8 (2), Trp not analyzed Example 50: Synthesis of Compound 55

Synthesis of the protected peptide was effected according to the same method as in Reference Example 1 except for using as a starting material 20 mg of a carrier resin to which 10.4 μmol of Fmoc-Trp was bound, and successively using as N-protected amino acids Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Phe-OH, Fmoc-Tyr(t-Bu)-OH, Fmoc-Val-OH, Fmoc-Ala-OH, Fmoc-Ala-OH, Fmoc-Ser(t-Bu)-OH, and Fmoc-Gly-OH. The peptide produced was separated from the resin by the same method as in Reference Example 1 to give 38.7 mg of the crude product. This crude product was purified by HPLC by the same method as in Reference Example 1 to give 5.6 mg of Compound 55.

Mass spectrography [FABMS]: 2272 (M+H)

Amino acid analysis: Found (Theoretical) Asx 1.6 (2), Ser 1.0 (1), Gly 1.0 (1), His 1.0 (1), Ala 3.0 (3), Tyr 1.5 (2), Val 1.4 (2), Ile 1.0 (2), Leu 1.1 (1), Phe 2.0 (2), Trp not analyzed Reference Example 1: Synthesis of Compound a
(H-Gly-Asn-Trp-His-Gly-Thr-Ala-Pro-Asp-Trp-Val-Tyr-Phe-Ala-His-Leu-Asp-Ile-Ile-Trp-OH: Sequence No. 42)

Following the synthesis program of Shimadzu Seisakusho, 20 mg of a carrier resin combined with 10.4 μmol of Fmoc-Trp was placed in the reactor of an automatic synthesizer, and the following procedure was effected.

(a) The carrier resin was washed with DMF for 3 minutes and the solution was drawn off.

(b) A 30% piperidine-DMF solution was added thereto, followed by stirring for 4 minutes. Then, the solution was drawn off, and this procedure was repeated again.

(c) The carrier resin was washed with DMF for one minute, the solution was drawn off, and this procedure was repeated 5 times.

Thus, a carrier resin to which Trp, a Fmoc group being removed therefrom, was bound was obtained.

(d) A mixture of 104 μmol Fmoc-Ile-OH, 104 μmol PyBOP, 104 μmol HOBt, and 156 μmol NMM was stirred for 3 minutes in 364 μl of DMF. The obtained solution was added to the resin, followed by stirring for 30 minutes, and then the solution was drawn off.

(e) The carrier resin was washed with DMF for one minute, and this procedure was repeated 5 times.

In this manner, Fmoc-Ile-Trp was synthesized on the carrier.

Next, after the washing and deprotective steps (a)–(c) above, a condensation reaction was effected using Fmoc-Ile-OH in step (d), and then Fmoc-Ile-Ile-Trp was synthesized on the carrier by way of the washing step (e). Steps (a)–(e) were repeated to give a carrier resin to which the protected peptide was bound, using successively in step (d) Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH. The carrier resin obtained by the further washing and deprotective steps (a)–(c) was washed with methanol and butyl ether, followed by drying for 3 hours under reduced pressure. A mixture solvent (300 μl) of TFA (90%), thioanisole (5%), and 1,2-ethanedithiol (5%) containing 2-methylindole in the proportion of 5 mg/ml was added thereto, followed by being allowed to stand at room temperature for 2 hours in order to remove side chain-protected groups and to separate the peptide produced from the resin. Then, the resin was filtered off, and about 3 ml of ether was added thereto to give 25 mg of the crude peptide by filtration. This crude peptide was purified by HPLC using a reverse phase column (CAPCELL PAK C18, 30 mmΦ× 250 mm, manufactured by Shiseido). The elution was effected with a linear concentration gradient pattern using 0–90% acetonitrile-water containing TFA (0.1%), and upon detection of 220 nm, fractions containing Compound a were obtained. These fractions were freeze-dried to give 21.8 mg of Compound a.

MS analysis [FABMS]: 2397 (M+H)

Amino acid analysis: Found (Theoretical) Gly 2.4 (2), Ala 2.0 (2), Asx 2.9 (3), His 1.9 (2), Ile 1.0 (2), Leu 0.9 (1), Phe 0.9 (1), Pro 1.1 (1), Thr 1.1 (1), Tyr 0.9 (1), Val 0.7 (1), Trp not analyzed Reference Example 2: Synthesis of Compound b (Compound b, SEQ ID NO.: 76)

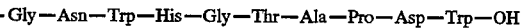

Gly—Asn—Trp—His—Gly—Thr—Ala—Pro—Asp—Trp—OH

Step 1: Synthesis of Compound h (Fmoc-Gly-Asn-Trp-His-Gly-Thr-Ala-Pro-OH: Sequence No. 43)

Following the synthesis program of ABI Co., 0.73 g of a carrier resin combined with 0.5 mmol of Boc-Pro was placed in the reactor of an automatic synthesizer, and the following procedure was effected.

(1) Treatment with a methylene chloride solution containing TFA (33%) (80 seconds)
(2) Treatment with a methylene chloride solution containing TFA (50%) (18.5 minutes)
(3) Washing with methylene chloride (3 times)
(4) Treatment with a methylene chloride solution containing diisopropylethylamine (10%) (one minute, 2 times)
(5) Washing with DMF (5 times)
(6) A DMF solution (4 ml) containing a symmetric acid anhydride of Boc-Ala (2.0 mmol) was added to the obtained carrier resin to which Pro was bound, followed by stirring for 18 minutes.
(7) Washing with methylene chloride (5 times)

Thus, Boc-Ala-Pro was synthesized on the carrier. Next, after the deprotective steps (1)–(5) above, a condensation reaction was effected using the symmetric anhydride of Boc-Thr(Bzl) in step (6), and then Boc-Thr(Bzl)-Ala-Pro was synthesized on the carrier resin by way of the washing step (7). Steps (1)–(7) were successively repeated to give 1.2 g of a carrier resin to which the protected peptide was bound. In step (6), Boc-Gly-OH, Boc-His(Bom)-OH, Boc-Trp (CHO)-OH, Boc-Asn-OH, and Fmoc-Gly-OH were successively used. To the obtained carrier resin were added 0.8 ml of 1,2-ethanedithiol, 0.8 ml of dimethylsulfide, and 0.2 ml of anisol, the mixture was allowed to stand for 3 hours, and 18 ml of hydrogen fluoride was added thereto, followed by stirring for 70 minutes under ice cooling. Next, hydrogen fluoride was removed off under reduced pressure, and 100 ml of ethyl acetate was added to the carrier resin, followed by stirring for 0.5 hour. To the carrier resin obtained by filtration was added 100 ml of DMF, followed by stirring for 1 hour. The carrier resin was then removed by a fully automatic high speed cooling centrifuge (RS-20 model, Tommy Seiko) at 10,000 rpm for 10 minutes to give a supernatant, and DMF was removed off from this supernatant using a concentrator (ROTARY VACUUM EVAPORATOR N-2 model, Tokyo Rika Kiki). The residue was dissolved in 2M acetic acid, and the resultant solution was freeze-dried to give 464.0 mg of the crude product. This crude product was purified by HPLC using a reverse phase column (CAPCELL PACK Ct8 SG-120, 30×250 mm). The elution was effected with a linear concentration gradient method using 0–100% water-acetonitrile containing TFA (0.1%), and upon detection at 220 nm, fractions containing the intended substances were obtained. These fractions were freeze-dried to give 131.9 mg of Compound h.

MS analysis: 1061 (M+H)

Amino acid analysis: Found (Theoretical): Asx 0.7 (1), Gly 2.1 (2), His 1.0 (1), Thr 1.0 (1), Pro 1.1 (1), Ala 1.1 (1), Trp not analyzed Step 2: Synthesis of H-Asp(Ot-Bu)-Trp-OBzl (a) Fmoc-Asp(Ot-Bu)-OH (41 mg) was dissolved in methylene chloride (1 ml), and then HONSu (12 mg) and DCC (21 mg) were added thereto at 0° C., followed by stirring at 0° C. for 30 minutes. A methylene chloride solution (1 ml) of H-Trp-OBzl hydrochloride (33 mg) and triethylamine (14 μl) were added to the solution, followed by stirring at 0° C. for 3 hours. The insoluble matters were filtered off, washed with cold methylene chloride, and the filtrate was recovered. The solvent was removed under reduced pressure and the residue was purified by silica gel column chromatography (WAKOGEL C-200, 50 g, eluted with chloroform/methanol=25/1) to give 167 mg of Fmoc-Asp(Ot-Bu)-Trp-OBz as a white powder.

MS analysis [FABMS]: 688 (M+H)

(b) The dipeptide (10 mg) obtained in (a) above was dissolved in DMF (3 ml), and then piperidine (0.75 ml) was added thereto, followed by being allowed to stand at room temperature for 10 minutes. Ether and hexane were added to the reaction solution, and the white crystals precipitated were collected by filtration and dried under reduced pressure to give 12 mg of H-Asp(Ot-Bu)-Trp-OBz.

MS analysis [FABMS]: 466 (M+H)

Step 3: Synthesis of Compound i (H-Gly-Asn-Trp-His-Gly-Thr-Ala-Pro-Asp-Trp-OBzl: Sequence No. 44)

(a) A DMF solution (5.5 ml) containing the dipeptide (1.7 mg) obtained in step 2 was added to Compound h (4.4 mg) obtained in step 1 and the mixture was cooled to 0° C. DEPC (0.5 µl) and triethylamine (1.0 µl) were successively added thereto, followed by stirring at 0° C. for 5 days. The solvent was removed under reduced pressure, and the residue was redissolved in 1 ml of DMF. The resultant solution was purified by HPLC using a reverse phase column (YMC-Pack ODS-AM, 150×6 mm I.D.) to give 320 µg of Fmoc-Gly-Asn-Trp-His-Gly-Thr-Ala-Pro-Asp(Ot-Bu)-Trp-OBzl (Sequence No. 45) as a white powder.

MS analysis [FABMS]: 1508 (M+H)

(b) To 250 µg of the protected peptide obtained in (a) above was added 50 µl of a solution from a mixture of 900 µl of TFA, 50 µl of 1,2-ethanedithiol, 50 µl of anisole, and 5 mg of methylindole, followed by being allowed to stand at room temperature for 1.5 hours. Ether was added to the solution, and the white precipitates produced were collected by filtration and dried. A 20% piperidine-DMF solution (100 µl) was added to the white precipitates, followed by being allowed to stand at room temperature for 15 minutes. Ether was added thereto again, and the white precipitates produced were collected by filtration and dried to give 200 µg of Compound i.

MS analysis [FABMS]: 1230 (M+H)

Step 4: Synthesis of Compound b (a) Compound i (66 µg) was dissolved in DMF (60 µl), and then a 0.1M DMF solution (1.6 µl) of PyBOP, a 0.1M DMF solution (1.6 µl) of HOBt, and a 1% DMF solution (3 µl) of NMM were added thereto at room temperature, followed by stirring at room temperature for 3 hours. The solvent was removed under reduced pressure, and the obtained product was purified by HPLC by the same method as in step 3 to give 20 µg of the benzyl ester of Compound b.

(b) The benzyl ester (250 µg) obtained in (a) above was dissolved in 80 µl of a mixture solvent of methanol and acetic acid in a ratio of 3/1, and then about 0.5 mg of 10% Pd/C was added thereto under nitrogen atmosphere. After changing the atmosphere to hydrogen atmosphere, the solution was stirred at room temperature for one hour. Pd/C was filtered off and ether was added to the filtrate. The white precipitates produced were collected by filtration and dried to give 100 µg of Compound b.

MS analysis [FABMS]: 1122 (M+H)

Amino acid analysis: Found (Theoretical): Gly 2.0 (2), Asx 1.7 (2), His 1.0 (1), Thr 1.0 (1), Ala 1.0 (1), Pro 1.0 (1), Trp not analyzed.

Reference Example 3: Synthesis of Compound c (Fmoc-Val-Tyr-Phe-Ala-His-Leu-Thr-Leu-Ile-OH: Sequence No. 46)

Synthesis of the protected peptide was effected according to the same method as in Reference Example 1 except for using as a starting material 294 mg of a carrier resin to which 73.5 µmol of Fmoc-Ile was bound, successively using as N-protected amino acids Fmoc-Leu-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, and Fmoc-Val-OH, and not effecting treatment with piperidine in step (b) in the final procedure for condensing Fmoc-Val-OH. The peptide produced was separated from the resin by using 10 ml of a mixture of TFA (90%), thioanisole (5%), and 1,2-ethanedithiol (5%), and allowing the mixture to stand at room temperature for 2 hours. The obtained crude product (72 mg) was purified by HPLC by the same method as in Reference Example 1 to give 43.6 mg of Compound c.

MS analysis [FABMS]: 1299 (M+H)

Reference Example 4: Synthesis of Compound d (Fmoc-Val-Tyr-Phe-Ala-His-Leu-Thr-Thi-Ile-OH: Sequence No. 47)

Synthesis of the protected peptide was effected according to the same method as in Reference Example 1 except for using as a starting material 294 mg of a carrier resin to which 73.5 µmol of Fmoc-Ile was bound, successively using as N-protected amino acids Fmoc-Thi-OH, Fmoc-Thr(t-Bu)-OH, Fmoc-Leu-OH, Fmoc-His(Trt)-OH, Fmoc-Ala-OH, Fmoc-Phe-OH, Fmoc-Tyr(t-Bu)-OH, and Fmoc-Val-OH, and not effecting treatment with piperidine in step (b) in the final procedure for condensing Fmoc-Val-OH. The peptide produced was separated from the resin by the same method as in Reference Example 3 to give 146 mg of the crude product. This crude product was purified by HPLC by the same method as in Reference Example 1 to give 61.7 mg of Compound d.

MS analysis [FABMS]: 1338 (M+H)

Reference Example 5: Synthesis of Compound u [H-Val-Tyr-Phe-Ala-His-Leu-Asp(OBzl)-Ile-Ile-Trp-OBzl: Sequence No. 61]

Step 1: Synthesis of Compound v [Fmoc-Val-Tyr-Phe-Ala-His-Leu-Asp(OBzl)-Ile-Ile-OH: Sequence No. 62]

Synthesis of the protected peptide was effected according to the same method as in Reference Example 1 except for using as a starting material 70 mg of a carrier resin to which 30.8 µmol of Fmoc-Ile was bound, successively using as N-protected amino acids Fmoc-Ile-OH, Fmoc-Asp(OBzl)-OH, Fmoc-Leu-OH, Fmoc-His(Trt)-OH, Fmoc-Ala-OH, Fmoc-Phe-OH, Fmoc-Tyr(t-Bu)-OH, and Fmoc-Val-OH, and not effecting treatment with piperidine in step (b) in the final procedure for condensing Fmoc-Val-OH. The peptide produced was separated from the resin by the same method as in Reference Example 1 to give 34.6 mg of the crude product of Compound v.

Step 2: Synthesis of Compound u (a) Compound v (2.0 mg) obtained in step 1 was dissolved in DMF (200 µl), and then a 42 mg/ml DMF solution (10 µl) of HOBt, a 162 mg/ml DMF solution (10 µl) of PyBOP, a 34.3 µl/ml DMF solution (10 µl) of NMM, and a 62 mg/ml DMF solution of H-Trp-OBzl hydrochloride were successively added thereto, followed by being allowed to stand at 4° C. for one day. The insoluble matters were filtered off and the filtrate was purified by HPLC by the same method as in step 2 of Example 47 to give 2.7 mg of the N-terminal-Fmoc-protected Compound u.

(b) To 2.7 mg of the peptide obtained in (a) above was added 100 µl of a 20% piperidine-DMF solution, followed by being allowed to stand at room temperature for 5 minutes. Diethyl ether was added to the solution. The crystals produced were washed with ether and dried under reduced pressure to give 467 µg of Compound u.

MS analysis [FABMS]: 1456 (M+H)

Reference Example 6: Synthesis of Compound w (H-Val-Tyr-Phe-Ser-His-Leu-Asp-Ile-Ile-Trp-OH: Sequence No. 63)

A carrier resin (1.5 g) combined with the protected peptide was obtained by the same method as in step 1 of Reference Example 2 except for using 0.71 g of carrier resin to which 0.5 mmol of Boc-Trp(CHO) was bound, and successively using as N-protected amino acids Boc-Ile-OH, Boc-Ile-OH, Boc-Asp(OBzl)-OH, Boc-Leu-OH, Boc-His (Bom)-OH, Boc-Ser(Bzl)-OH, Boc-Phe-OH, Boc-Tyr(Br-Z)-OH, and Boc-Val-OH. With regard to 0.8 g of the obtained carrier resin, the peptide produced was separated from the resin by treatment with hydrogen fluoride, and dissolved in 2M acetic acid. The resultant solution was freeze-dried to give 243.3 mg of the crude product. With regard to 101 mg of the crude product, the crude product was purified by HPLC by the same method as in step 1 of Reference Example 2 to give 7.0 mg of Compound w.

MS analysis [FABMS]: 1292 (M+H)

Amino acid analysis: Found (Theoretical) Asx 1.1 (1), Ser 1.1 (1), His 1.2 (1), Tyr 1.0 (1), Val 1.0 (1), Ile 1.5 (2), Leu 1.2 (1), Phe 1.1 (1), Trp not analyzed Industrial Applicability According to the present invention, there can be provided a novel peptide which has endothelin-antagonizing activity, and is useful for treatment of hypertension, asthma, cerebral apoplexy, angina pectoris, actute renal insufficiency, cardiac infarction, cerebral vasospasm, etc.

What is claimed is:

1. A peptide compound represented by the following formula:

$R^1$-$R^2$-$R^3$-$R^4$-$R^5$-$R^6$-$R^7$-$R^8$-$R^9$-$R^{10}$-$R^{11}$-$R^{12}$-Phe-$R^{14}$-$R^{15}$-$R^{16}$-$R^{17}$-$R^{18}$-Ile-$R^{20}$-Z  SEQ ID NO. 64 wherein $R^1$ represents

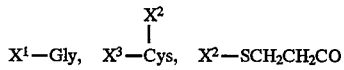

or hydrogen;

$R^2$ represents Asn, Asp, Phe, Tyr, Ser, or a single bond;

$R^3$ represents Trp, Ile, Pro, Ala, or a single bond;

$R^4$ represents His, Lys, Gly, Trp, Ala, or a single bond;

$R^5$ represents Gly, Thr, Trp, Val, or a single bond;

$R^6$ represents Gly, Thr, Asn, Tyr, Asp, or a single bond;

$R^7$ represents Ala, Ser, Asn, Asp, Tyr, Phe, or a single bond;

$R^8$ represents Pro, Ala, Arg, or a single bond;

$R^9$ represents

or a single bond;

$R^{10}$ represents Trp or Ala;

$R^{11}$ represents Val, Pro, or a single bond;

$R^{12}$ represents Tyr or a single bond;

$R^{14}$ represents Ala, MeAla, Ser, or Cys;

$R^{15}$ represents His or Trp;

$R^{16}$ represents Leu or Nva;

$R^{17}$ represents Asp, Thr, Asn, Ser, Gly, or Glu;

$R^{18}$ represents Ile, Leu, Cha, Abu, Thi, Met, Tyr, MeLeu, MeIle, Phg, or Nle;

$R^{20}$ represents Trp, Phe, or Tyr; and

Z represents hydroxy, lower alkoxy, or amino (wherein $X^1$ and $X^3$ each represent hydrogen, benzyloxycarbonyl, t-butyloxycarbonyl, 9-fluorenylmethyloxycarbonyl, or carboxy-substituted or unsubstituted lower alkanoyl; $X^2$ represents hydrogen or acetamidomethyl; $Y^1$ represents hydroxy or lower alkoxy; $Y^2$ represents hydrogen, or $X^1$ and $Y^1$ or $X^2$ and $Y^2$ are combined together to form a single bond as $X^1$-$Y^1$ or $X^2$-$Y^2$; and Nva represents a norvaline residue, Cha represents a β-cyclohexylalanine residue, Abu represents a 2-aminobutanoic acid residue, Thi represents a β-(2-thienyl)alanine residue, Phg represents a phenylglycine residue, Nle represents a norleucine residue, MeAla represents a N-methylalanine residue, MeLeu represents a N-methylleucine residue, MeIle represents a N-methylisoleucine residue, and amino acid residues other than Gly each represent a D-, L-, or DL-amino acid residue, or a pharmaceutically acceptable salt thereof.

2. A peptide compound represented by the following formula:

$R^1$-$R^2$-$R^3$-$R^4$-$R^5$-$R^6$-$R^7$-$R^8$—$R^9$-Trp-Val-Tyr-Phe-Ala-His-Leu-$R^{17}$-$R^{18}$-Ile-Trp-OH SEQ ID NO.: 65, wherein $R^1$, $R^2$, $R^3$, $R^4$, $R^5$, $R^6$, $R^7$, $R^8$, $R^9$, $R^{17}$ and $R^{18}$ have the same meanings as defined in claim 1, or a pharmaceutically acceptable salt thereof.

3. A peptide compound represented by the following formula:

$$\overset{Y^1}{\underset{|}{X^1-Gly-Asn-Trp-His-Gly-Thr-Ala-Pro-Asp-Trp-Val-Tyr-Phe-Ala-His-Leu-R^{17}-R^{18}-Ile-Trp-OH}} \quad \text{SEQ ID NO.: 66,}$$

wherein $R^{17}$, $R^{18}$, $X^1$ and $Y^1$ have the same meanings as defined in claim 1, or a pharmaceutically acceptable salt thereof.

4. H-Gly-Asn-Trp-His-Gly-Thr-Ala-Pro-Asp-Trp-Val-Tyr-Phe-Ala-His-Leu-Ser-Met-Ile-Trp-OH, SEQ ID NO.: 21, H-Gly-Asn-Trp-His-Gly-Thr-Ala-pro-Asp-Trp-Val-Tyr-Phe-Ala-His-Leu-Thr-Thi-Ile-Trp-OH, SEQ ID NO.: 17; H-Gly-Asn-Trp-His-Gly-Thr-Ala-Pro-Asp-Trp-Val-Tyr-Phe-Ala-His-Leu-Thr-Cha-Ile-Trp-OH, SEQ ID NO.: 14 H-Gly-Asn-Trp-His-Gly-Thr-Ala-pro-Asp-Trp-Val-Tyr-Phe-Ala-His-Leu-Thr-Met-Ile-Trp-OH, SEQ ID NO.: 18; HOOCCH$_2$CH$_2$CO-Gly-Asn-Trp-His-Gly-Thr-Ala-Pro-AsP-Trp-Val-Tyr-Phe-Ala-His-Leu-Asp-Ile-Ile-Trp-OH, SEQ ID NO.: 1; H-Gly-Asn--Trp-His-Gly-Thr-Ala-pro-Asp-Trp-Val-Tyr-Phe-Ala-His-Leu-Thr-Leu-Ile-Trp-OH, SEQ ID NO.: 13; or a pharmaceutically acceptable salt thereof.

5.

$$\overline{\text{Gly-Asn-Trp-His-Gly-Thr-Ala-Pro-Asp-Trp-Val-Tyr-Phe-Ala-His-Leu-Thr-Thi-Ile-Trp-OH}}, \quad \text{SEQ ID NO.: 68;}$$

$$\overline{\text{Gly-Asn-Trp-His-Gly-Thr-Ala-Pro-Asp-Trp-Val-Tyr-Phe-Ala-His-Leu-Thr-Leu-Ile-Trp-OH}}, \quad \text{SEQ ID NO.: 69;}$$

or a pharmaceutically acceptable salt thereof.

6. A peptide compound represented by the following formula:

$$\text{H-Cys-Asn-Trp-His-Gly-Thr-Ala-Pro-Cys-Trp-Val-Tyr-Phe-Ala-His-Leu-}R^{17}\text{-}R^{18}\text{-Ile-Trp-OH} \quad \text{(SEQ ID NO.: 67)}$$

wherein $R^{17}$ and $R^{18}$ have the same meanings as defined in claim 1, or a pharmaceutically acceptable salt thereof.

7.

SEQ ID NO.: 30;

H—Cys—Asn—Trp—His—Gly—Thr—Ala—Pro—Cys—Trp—Val—Tyr—Phe—Ala—His—Leu—Asp—Ile—Ile—Trp—OH,
(disulfide bond between Cys-Cys)

SEQ ID NO.: 34;

H—Cys—Asn—Trp—His—Gly—Thr—Ala—Pro—Cys—Trp—Val—Tyr—Phe—Ala—His—Leu—Thr—Leu—Ile—Trp—OH,
(disulfide bond between Cys-Cys)

SEQ ID NO.: 36;

H—Cys—Asn—Trp—His—Gly—Thr—Ala—Pro—Cys—Trp—Val—Tyr—Phe—Ala—His—Leu—Thr—Cha—Ile—Trp—OH,
(disulfide bond between Cys-Cys)

or a pharmaceutically acceptable salt thereof.

8.

SEQ ID NO.: 71

Gly—Phe—Ile—Gly—Trp—Gly—Asn—Asp—Trp—Val—Tyr—Phe—Ala—His—Leu—Asp—Ile—Ile—Trp—OH,
(cyclic)

SEQ ID NO.: 72;

Gly—Tyr—Pro—Trp—Trp—Asn—Tyr—Arg—Asp—Trp—Val—Tyr—Phe—Ala—His—Leu—Asp—Ile—Ile—Trp—OH,
(cyclic)

SEQ ID NO.: 73;

Gly—Ser—Ala—Ala—Val—Tyr—Phe—Asp—Trp—Val—Tyr—Phe—Ala—His—Leu—Asp—Ile—Ile—Trp—OH,
(cyclic)

or a pharmaceutically acceptable salt thereof.

9. A pharmaceutical composition comprising a pharmaceutically acceptable carrier and as an active ingredient, an effective amount of the compound as defined by any of claims 1 to 8.

* * * * *